(12) United States Patent
Provenzani et al.

(10) Patent No.: US 10,689,342 B2
(45) Date of Patent: Jun. 23, 2020

(54) AZA-TANSHINONE DERIVATIVES, PROCESS FOR THEIR PREPARATION AND THEIR USE IN THERAPY

(71) Applicants: UNIVERSITA' DEGLI STUDI DI MILANO, Milan (IT); UNIVERSITA' DEGLI STUDI DI TRENTO, Trento (IT); UNIVERSITA' DEGLI STUDI DI NAPOLI FEDERICO II, Naples (IT)

(72) Inventors: Alessandro Provenzani, Trento (IT); Vito Giuseppe D'Agostino, Trento (IT); Natthakan Thongon, Trento (IT); Chiara Zucal, Trento (IT); Preet Lal, Trento (IT); Valentina Adami, Trento (IT); Pierfausto Seneci, Desenzano (IT); Leonardo Manzoni, Lissone (IT); Luciana Marinelli, Naples (IT); Ettore Novellino, Naples (IT); Marco Fragai, Sesto Fiorentino (IT); Claudio Luchinat, Florence (IT); Linda Cerofolini, Impruneta (IT); Carmelo Fuccio, Paolisi (IT)

(73) Assignee: UNIVERSITA' DEGLI STUDI DI TRENTO, Trento (IT)

( * ) Notice: Subject to any disclaimer, the term of this patent is extended or adjusted under 35 U.S.C. 154(b) by 0 days.

(21) Appl. No.: 16/310,102

(22) PCT Filed: Jun. 14, 2017

(86) PCT No.: PCT/IB2017/053519
§ 371 (c)(1),
(2) Date: Dec. 14, 2018

(87) PCT Pub. No.: WO2017/216732
PCT Pub. Date: Dec. 21, 2017

(65) Prior Publication Data
US 2019/0241516 A1 Aug. 8, 2019

(30) Foreign Application Priority Data
Jun. 14, 2016 (IT) .............................. UA2016A4369

(51) Int. Cl.
| | |
|---|---|
| *C07D 209/08* | (2006.01) |
| *A61P 37/00* | (2006.01) |
| *A61P 25/28* | (2006.01) |
| *A61P 31/12* | (2006.01) |
| *A61P 35/02* | (2006.01) |
| *A61K 45/06* | (2006.01) |

(52) U.S. Cl.
CPC ............ *C07D 209/08* (2013.01); *A61P 25/28* (2018.01); *A61P 31/12* (2018.01); *A61P 35/02* (2018.01); *A61P 37/00* (2018.01); *A61K 45/06* (2013.01)

(58) Field of Classification Search
CPC ................................ C07D 209/08; A61P 25/28
See application file for complete search history.

*Primary Examiner* — Golam M Shameem
(74) *Attorney, Agent, or Firm* — Silvia Salvadori

(57) ABSTRACT

Object of the present invention are new aza-tanshinone derivatives, a method for their preparation and their use in therapy, particularly, but not limited to, as anti-tumor agents and anti-inflammatories. The invention comprises also the pharmaceutical compositions containing them.

11 Claims, No Drawings

AZA-TANSHINONE DERIVATIVES, PROCESS FOR THEIR PREPARATION AND THEIR USE IN THERAPY

This application is a U.S. national stage of PCT/IB2017/053519 filed on 14 Jun. 2017, which claims priority to and the benefit of Italian Application No. UA2016A004669 filed on 14 Jun. 2016, the contents of which are incorporated herein by reference in their entireties.

SUMMARY OF THE INVENTION

Object of the present invention are new aza-tanshinone derivatives, a method for their preparation and their use in therapy, particularly, but not limited to, as anti-tumor agents and anti-inflammatories. The invention comprises also the pharmaceutical compositions containing them.

TECHNICAL BACKGROUND

The human antigen R, called HuR, (Humans antigen R), encoded by the ELAVL1 gene, is a RNA binding protein (RBP, RNA binding protein) with an important role in various post-transcriptional events for thousands of coding and non-coding RNAs. HuR is one of the most important elements of trans (trans-acting factors) type which recognizes, with high affinity, AU rich sequences (AREs) and modulates the half-lives of target RNAs, their translatability, the splicing and their localization. In this way, indirectly, it modulates the protein synthesis.

In normal tissues, the HuR activity is critical to guarantee the cell survival, differentiation and proliferation. High HuR levels have been associated with aggressive breast, ovarian, urothelium, bladder, intestine and lung cancers, which show more serious progression and for which an accumulation of cytoplasmic HuR is correlated with an adverse prognosis for patients. The HuR deregulation has been also correlated with inflammatory diseases and tumor diseases, where a physiological alteration of its target RNAs has been observed.

Compounds supposed to be able to inhibit the interaction between HuR and mRNA have been prepared in the past, however they have not provided the desired results. Dihydrotanshinone, of the following formula:

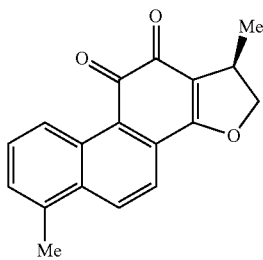 [SMILES: Cc1cccc2c3c(ccc12)C1=C(C(=O)C3=O)[C@@H](C)CO1]

is a natural product derived from Danshen (*Salvia miltiorrhiza* Bunge), widely used in Asia for the treatment of inflammatory diseases, which has been recently described as having anti-tumor activity. Its activity mechanism, however, has not been elucidated to date.

OBJECTS OF THE INVENTION

It is an object of the present invention to provide new aza-tanshinone derivatives useful in therapy, for a variety of diseases. In particular, but not limited to, in the anti-tumor and anti-inflammatory therapies.

It is another object of the present invention to provide a method for the preparation of said new derivatives, and their use in therapy, advantageously in the form of pharmaceutical compositions.

DESCRIPTION OF THE INVENTION

Object of the invention, according to one of the aspects thereof, is a compound of formula (I)

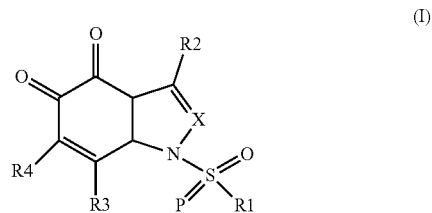

or a salt, solvate or hydrate thereof, wherein:

$R_1$ is:
   $C_{1-8}$ alkyl or heteroalkyl; $C_{2-6}$ alkenyl or heteroalkenyl; $C_{2-6}$ alkynyl or heteroalkynyl, all of them being optionally substituted;
   aryl, alkylaryl, heteroaryl, or alkylheteroaryl, all of them being optionally substituted;

$R_2$, $R_3$, $R_4$ are, each independently:
   a hydrogen atom;
   $C_{1-8}$ alkyl or heteroalkyl; $C_{2-6}$ alkenyl or heteroalkenyl; $C_{2-6}$ alkynyl or heteroalkynyl, all of them being optionally substituted;
   aryl, alkylaryl, heteroaryl, or alkylheteroaryl, all of them being optionally substituted;
   or $R_3$ and $R_4$, together with the carbon atoms to which they are bound, form a 5 or 6 membered cycloalkyl, cycloheteroalkyl, aryl or heteroaryl ring being optionally substituted, being optionally fused with one or more other rings.

X is C—$R_5$ or N;
$R_5$ is:
   a hydrogen atom;
   $C_{1-6}$ alkyl or heteroalkyl; $C_{2-6}$ alkenyl or heteroalkenyl; $C_{2-6}$ alkynyl or heteroalkynyl, all of them being optionally substituted.

According to the present invention, the alkyl, heteroalkyl, alkenyl, heteroalkenyl, alkynyl and heteroalkynyl groups can be straight or branched. Preferred groups according to the invention are methyl, ethyl, propyl, isopropyl, butyl, tert-butyl, ethenyl, propenyl, isopropenyl, butenyl, isobutenyl, ethenyl, ethynyl, propynyl and butynyl.

Preferred chains are $C_{1-4}$ alkyl or heteroalkyl, $C_{2-4}$ alkenyl or heteroalkenyl and $C_{2-4}$ alkynyl or heteroalkynyl.

The prefix "hetero" means that one or more carbon atoms in the chain or ring are replaced by one or more atoms independently selected from O, S and N.

The term aryl preferably denotes optionally substituted phenyl and naphthyl, more preferably phenyl and substituted phenyl.

The term heteroaryl preferably denotes a 5 to 10 membered monocycle, a polycycle or a fused ring of heterocyclic aromatic type containing 1 to 4 heteroatoms selected from oxygen atom, sulfur atom and nitrogen atom as ring constituents. Examples include, e.g., the furyl group, the thienyl group, the pyrrolyl group, the oxazolyl group, the isoxazolyl group, the thiazolyl group, the isothiazolyl group, the imidazolyl group, the pyrazolyl group, the oxadiazolyl group, the thiadiazolyl group, the triazolyl group, the tetrazolyl group, the pyridyl group, the pyrimidyl group, the pyrazinyl group, the pyridazinyl group, the benzofuranyl group, the isobenzofuranyl group, the benzothienyl group, the indolyl group, the isoindolyl group, the indazolyl group, the benzimidazolyl group, the benzoxazolyl group, the benzisoxazolyl group, the benzothiazolyl group, the benzoisothiazolyl group, the benzoxadiazolyl group, the benzothiadiazolyl group, the benzotriazolyl group, the quinolinyl group, the isoquinolinyl group, the cinnolyl group, the quinazolyl group, the quinoxalynyl group, the phthalazinyl group, the naphthyridinyl group, the purinyl group, the pteridinyl group, the furopyridyl group, the thienopyridyl group, the pyrrolopyridyl group, the oxazolpyridyl group, the thiazopyridyl group, the imidazopyridyl group, and the like. Any substitution is possible, provided that it provides a chemically stable molecule.

Preferred substitutions are for example a halogen, for example chlorine and fluorine; an alkoxy, for example methoxy; a hydroxy; an alkylhydroxy; an amine; a substituted amine for example with one or two alkyls; an alkylamine; an amide; an alkylamide; a carboxyl; an ester; a cyano a nitro; an oxo group; a thioxo group; and a trifluoromethyl. However other substitutions are possible; preferred substitutions are reported in the compounds of the following examples.

Preferably $R_1$ is an alkyl or an aryl group, optionally substituted, advantageously phenyl.

Preferably $R_2$ is hydrogen or an alkyl or an aryl group, advantageously phenyl, all being optionally substituted.

Preferable X is a CH group or a nitrogen.

When $R_3$ and $R_4$ form a cycle, preferred cycles are decalin, or a dehydrodecalin, which are optionally substituted; a naphthalene, optionally substituted; a dihydronaphthalene, optionally substituted; a cyclohexane or a cyclohexene, which are optionally substituted; an optionally substituted benzene; and bridged cycles, such as bicyclo (2.2.2)oct-2-ene.

Salts of the compounds of formula (I) include, e.g., acid addition salts, base addition salts, and the like. Specifically, examples of acid addition salts include acid addition salts with an inorganic acid such as hydrochloride, hydrobromide, hydroiodide, sulfate, nitrate and phosphate; and acid addition salts with an organic acid such as benzoate, methanesulfonate, ethanesulfonate, benzenesulfonate, p-toluenesulfonate, maleate, fumarate, tartrate, citrate and acetate. Examples of base addition salts include base addition salts with a metal such as sodium salt, lithium salt, calcium salt and magnesium salt; salts with an amine such as ammonium, trimethylamine, triethylamine, pyridine, collidine and lutidine; base addition salts with an organic base such as lysine and arginine, and the like.

Preferred salts according to the invention are the pharmaceutically acceptable salts. Prodrugs of the compounds of the invention are also an object of the present invention, where prodrug is meant to denote a compound which releases the compound of the invention into the organism following its metabolization.

The compounds of the invention can be prepared by means of methods known in the art. General procedures and detailed synthesis are however reported in the Experimental Section of the present description.

Preferred compounds have the following structures:

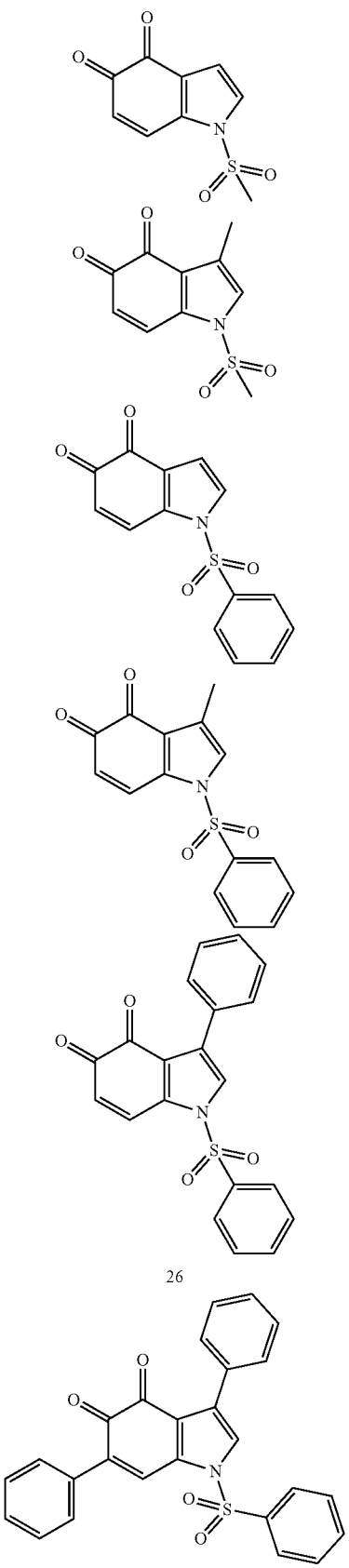

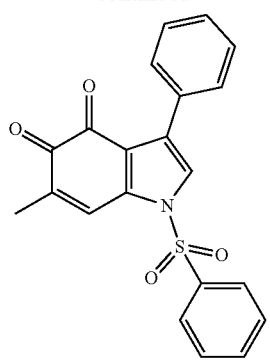
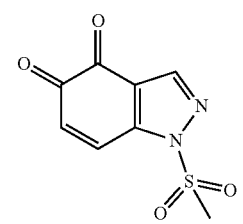
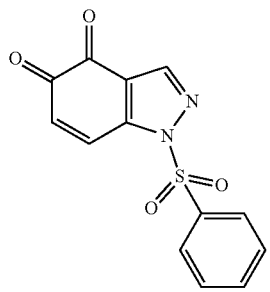
22
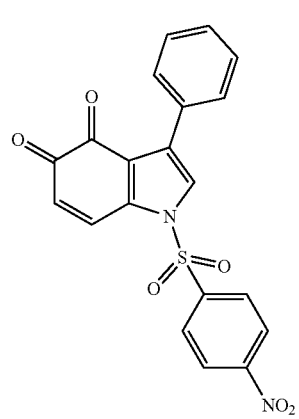
23
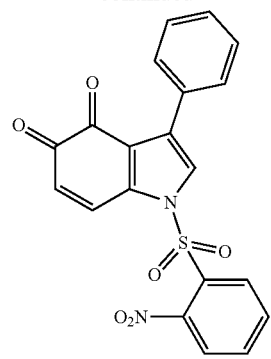
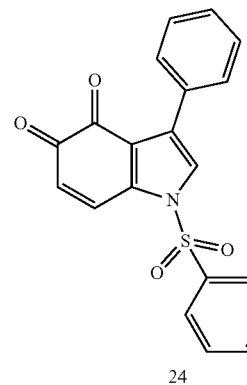
24
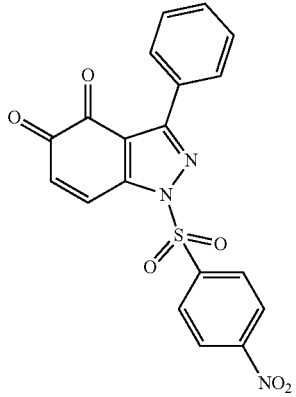
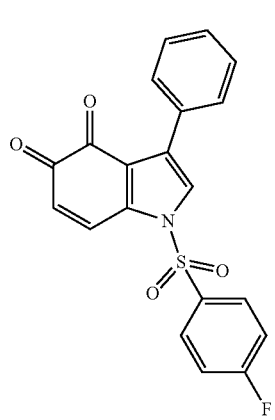
25

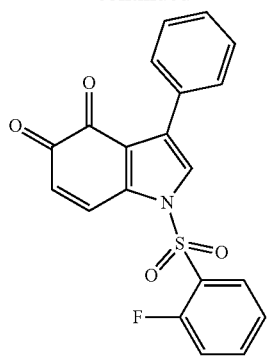
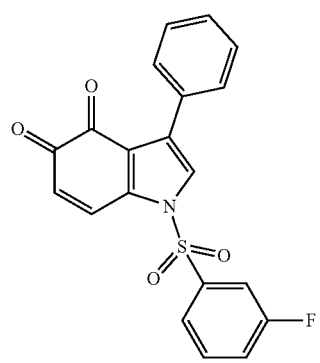
27
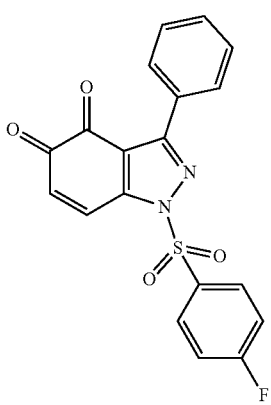
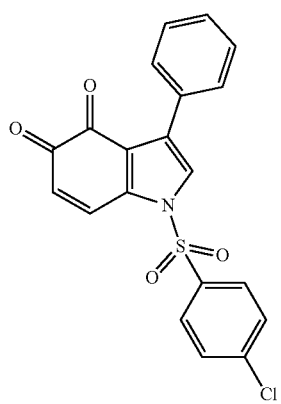
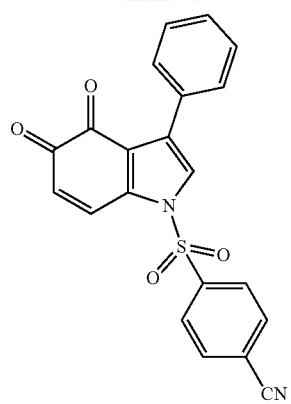
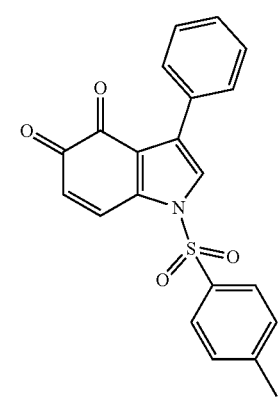
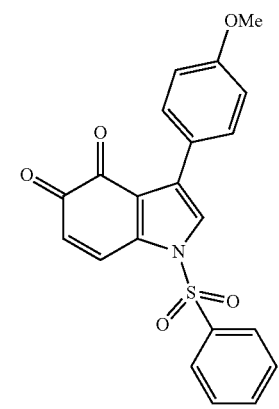
28
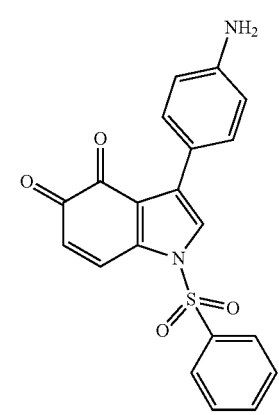

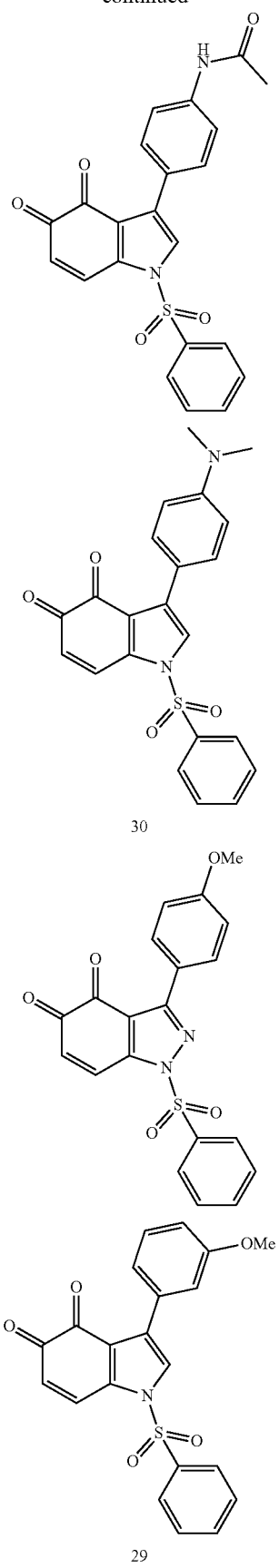
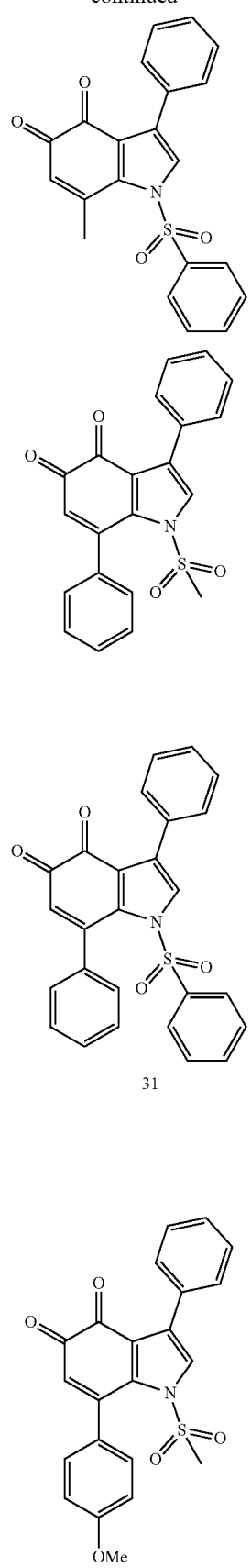

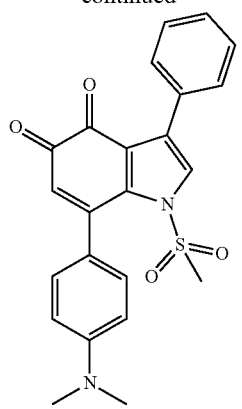
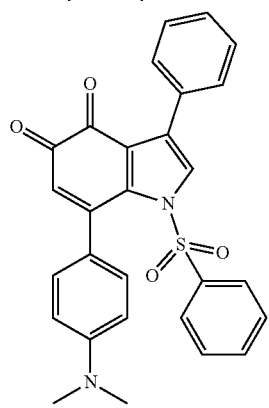
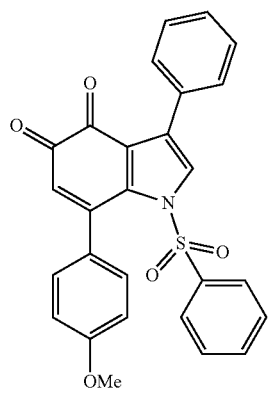
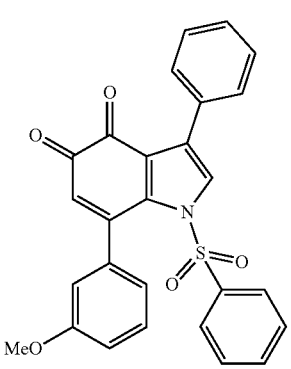
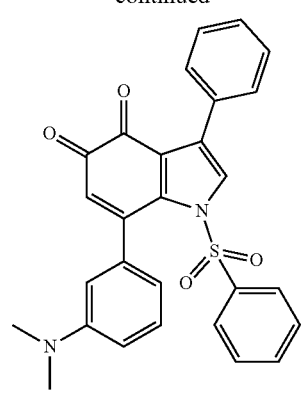
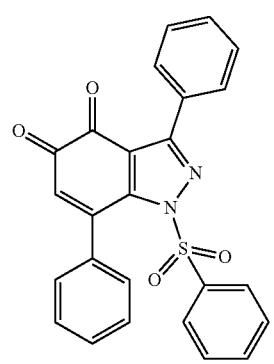
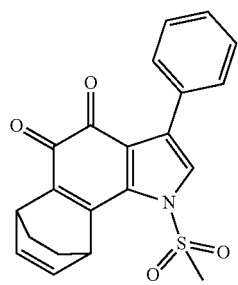
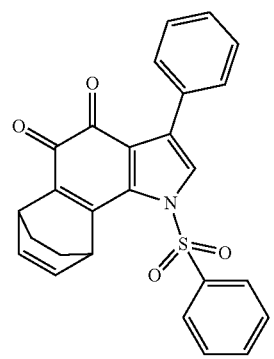

-continued
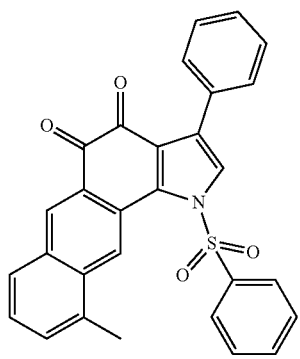
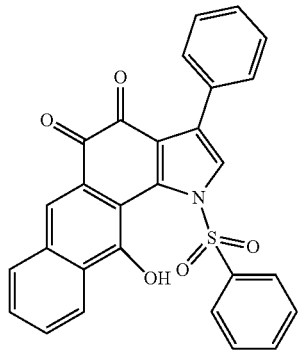
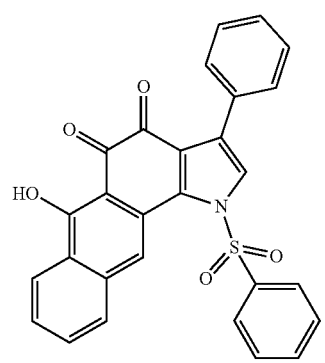
33
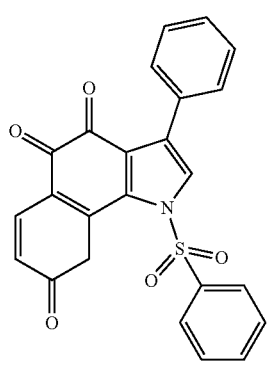
-continued
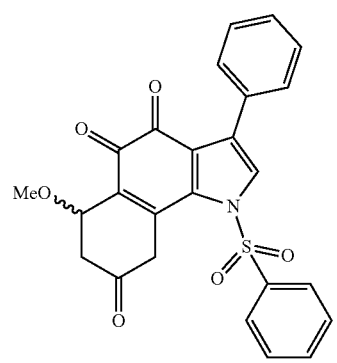
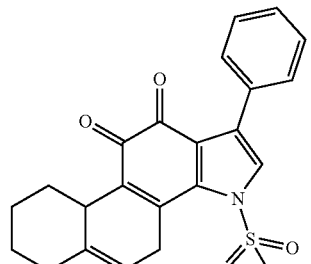
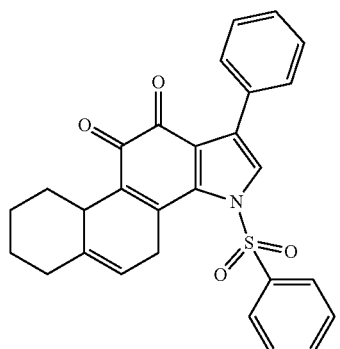
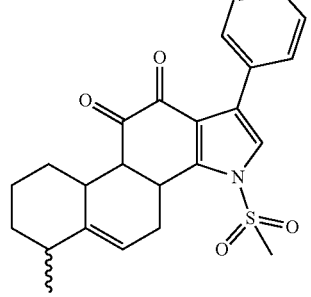
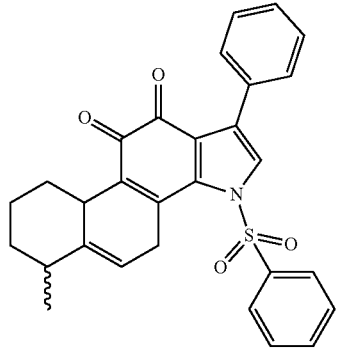

15
-continued
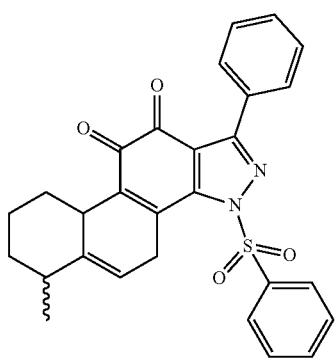
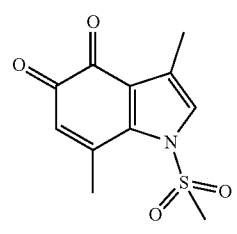
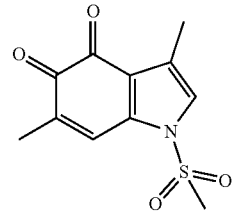
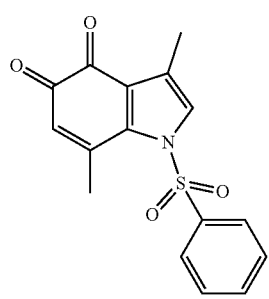
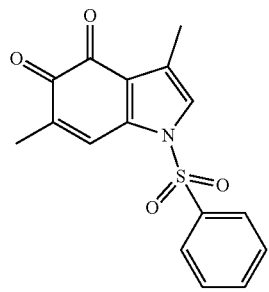
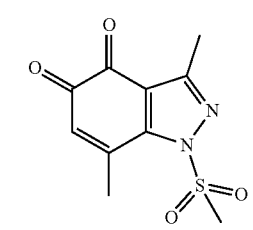
16
-continued
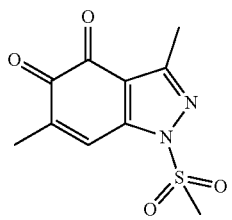
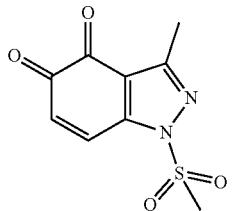
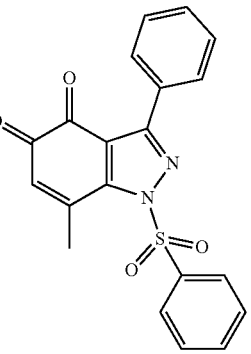
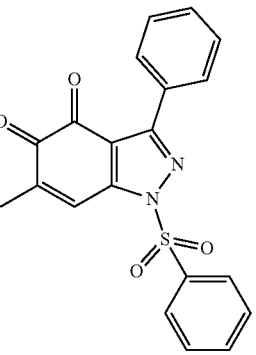
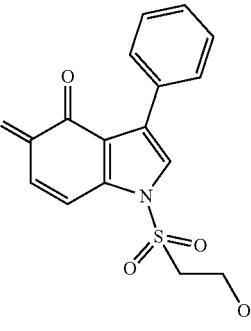

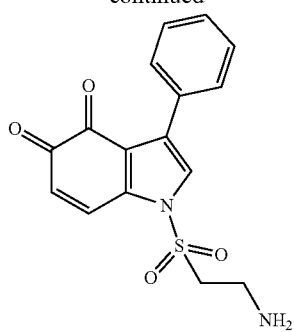
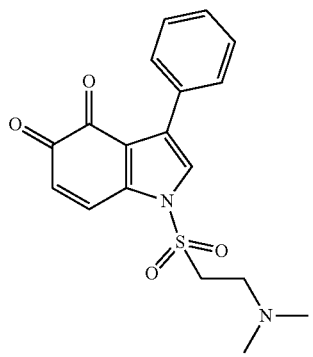
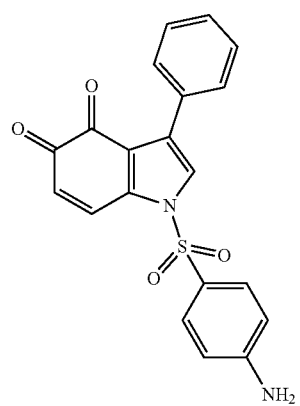
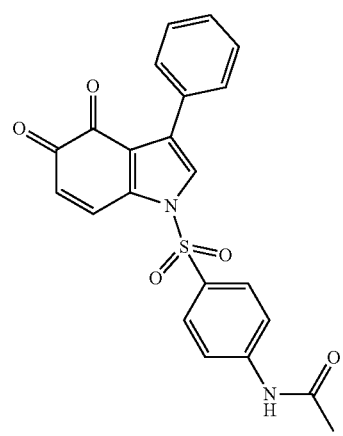
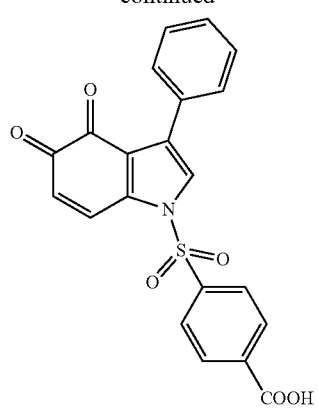
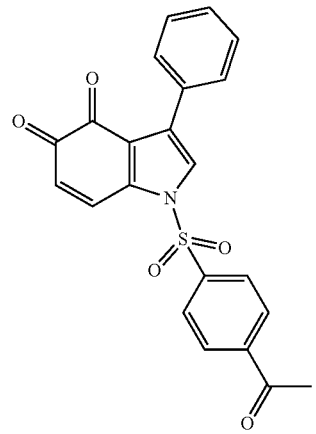
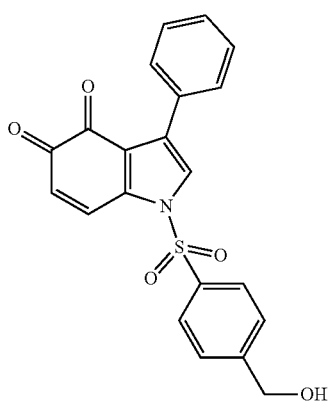
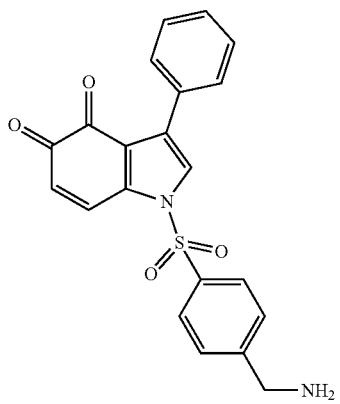

-continued
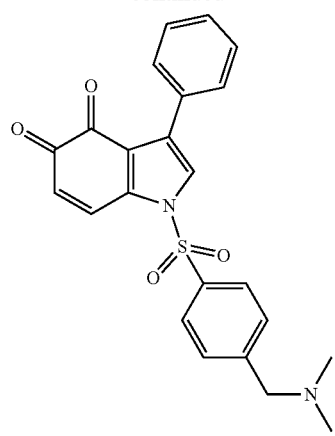
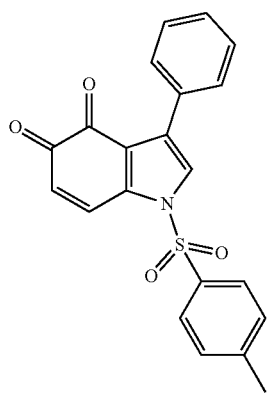
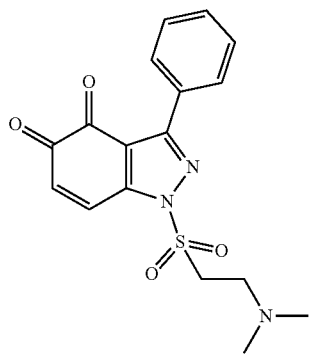
-continued
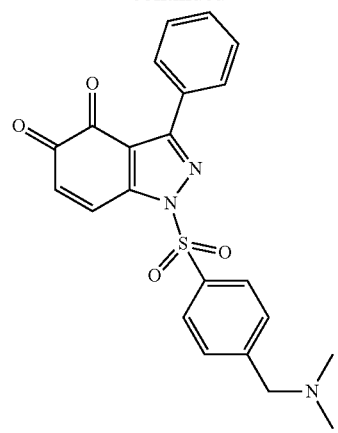
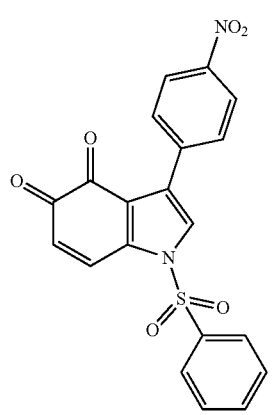
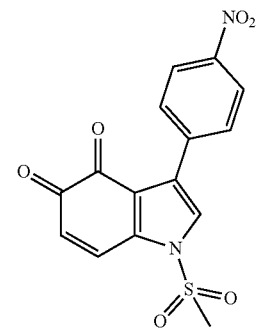
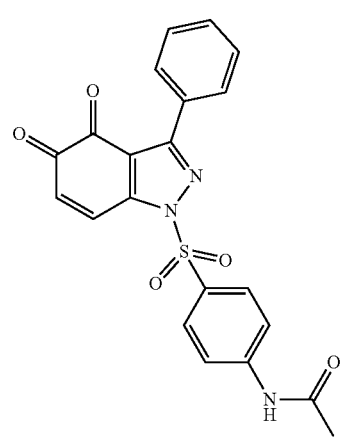
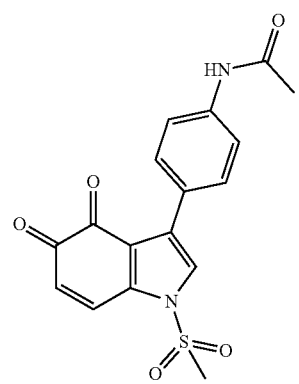

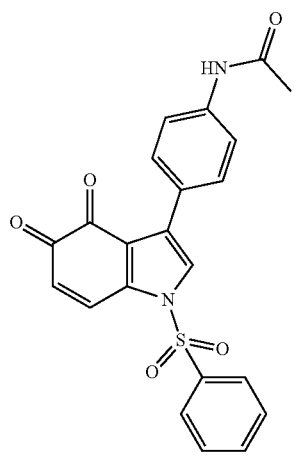
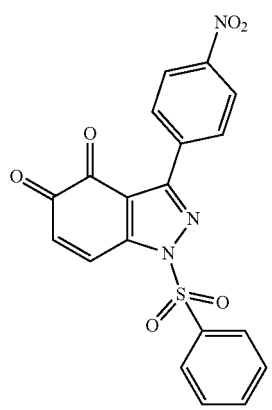
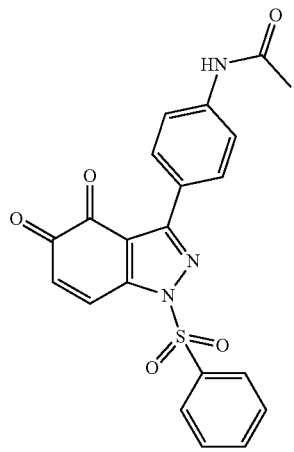
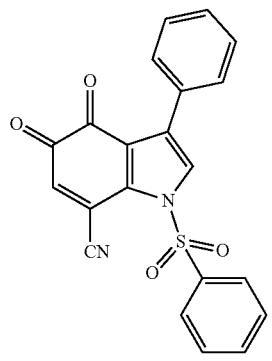
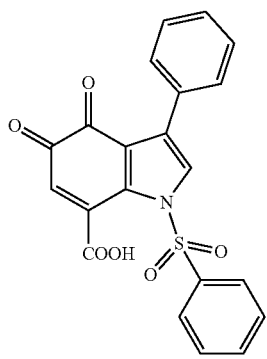
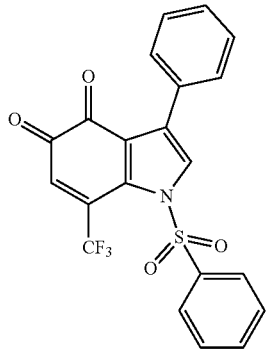
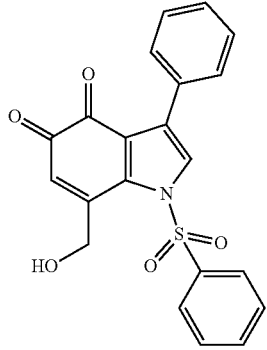
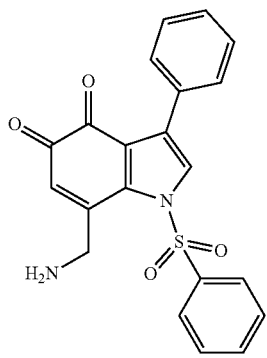

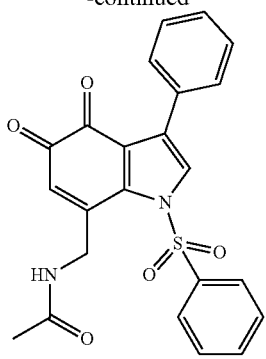
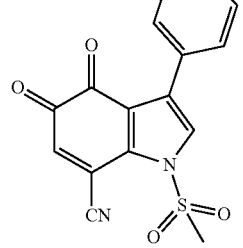
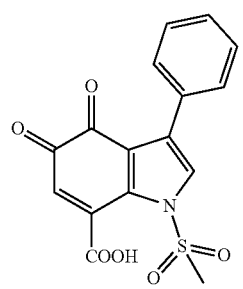
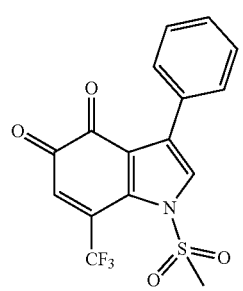
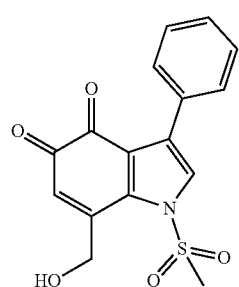
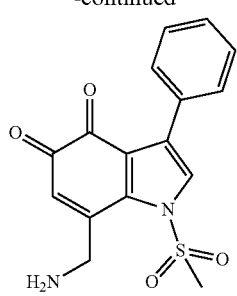
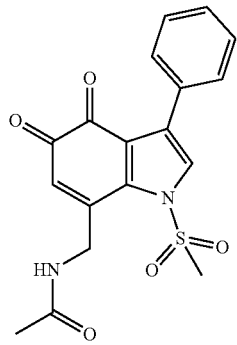
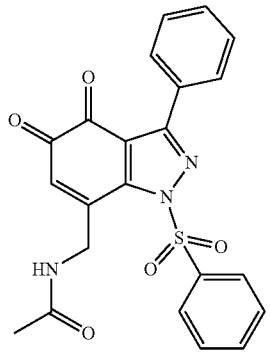
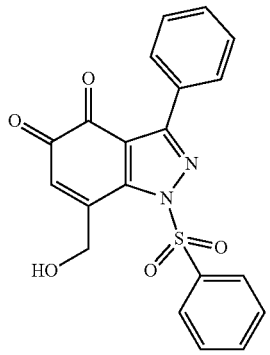
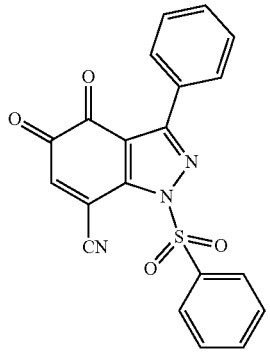

-continued
25
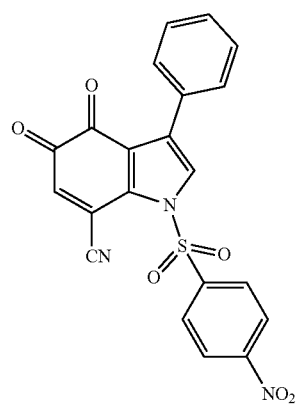
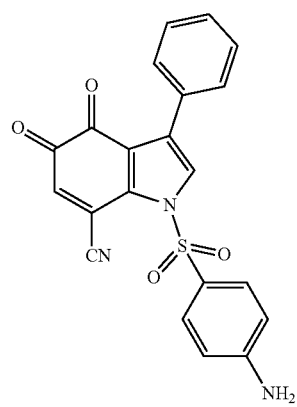
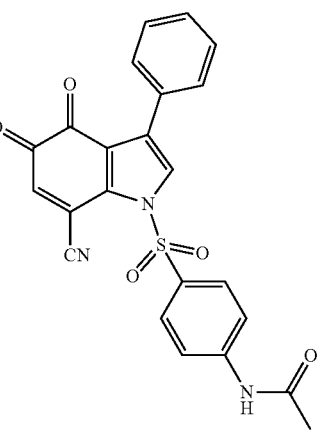
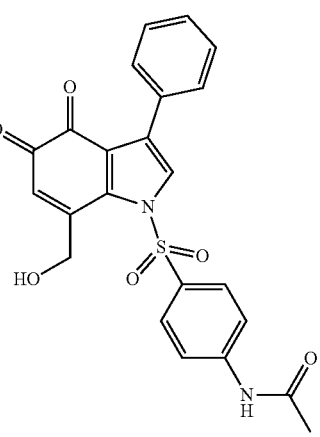
26
-continued
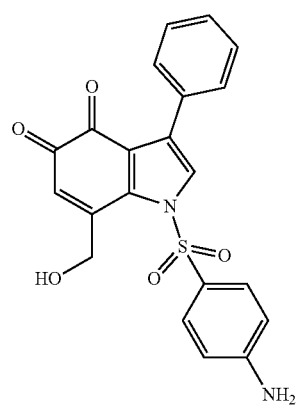
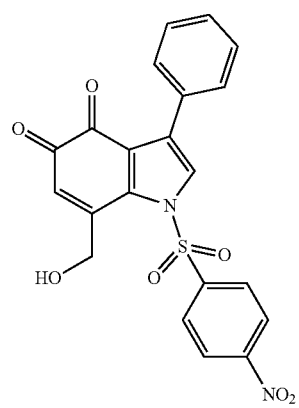
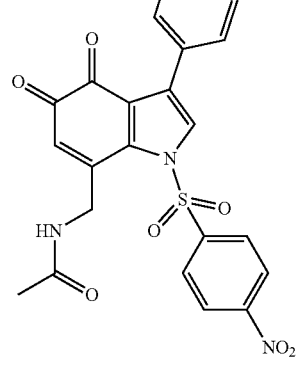
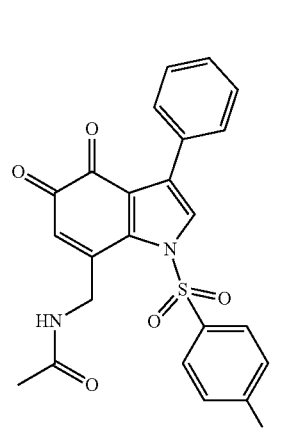

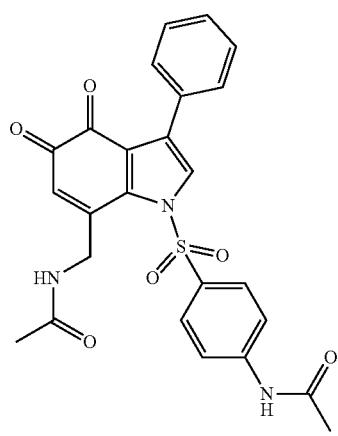
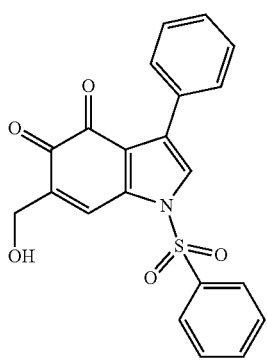
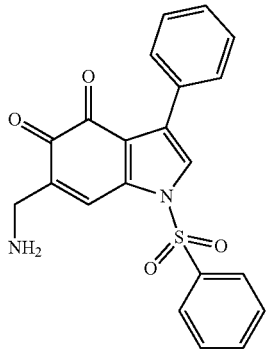
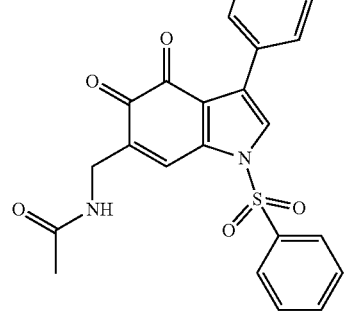
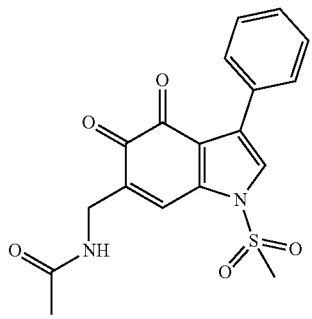
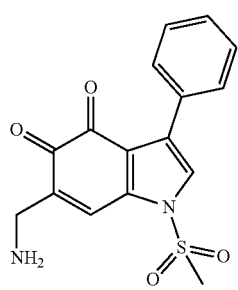

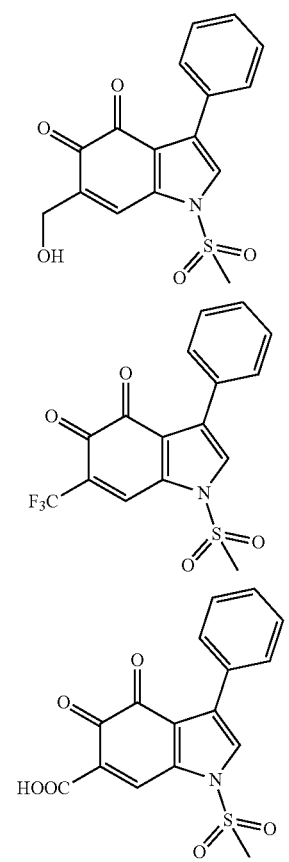
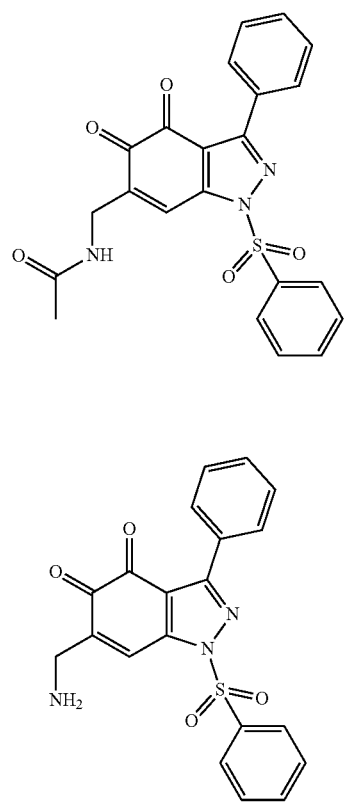

31
-continued
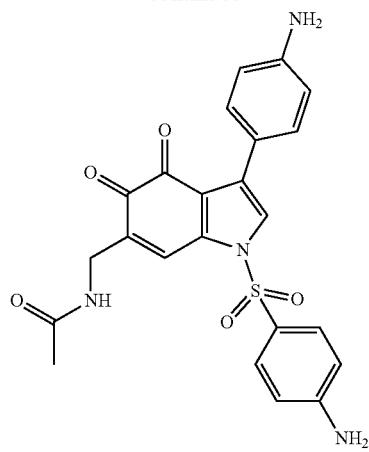
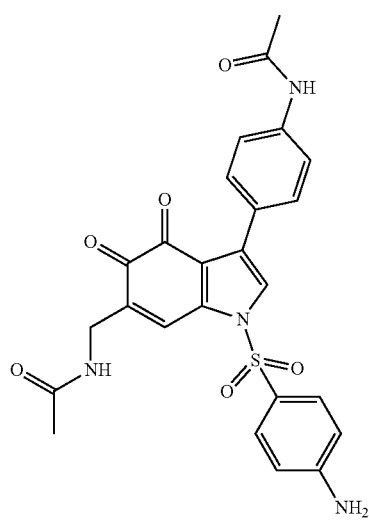
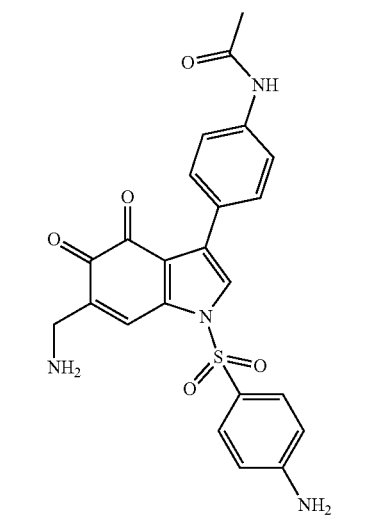
32
-continued
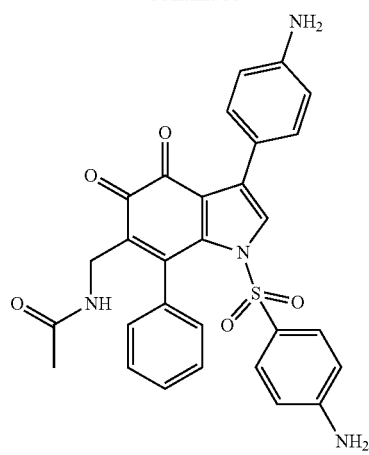
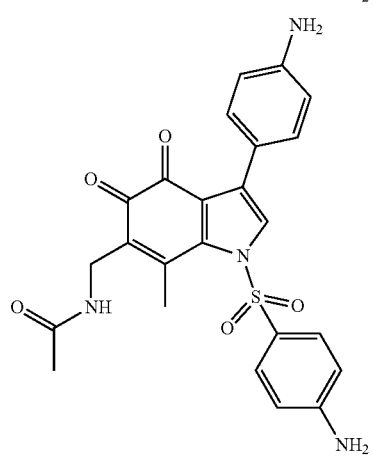
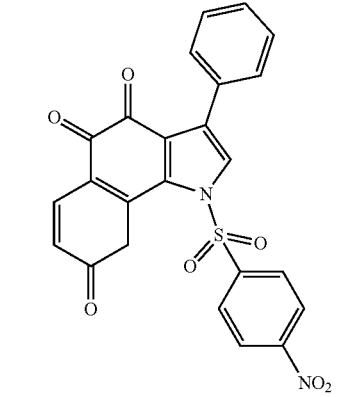
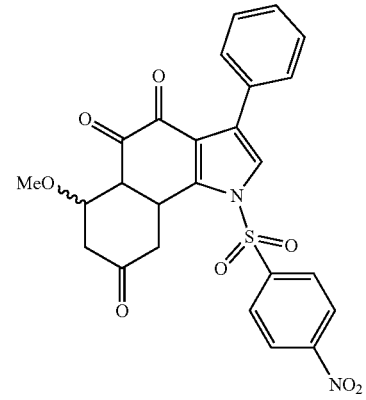

33
-continued
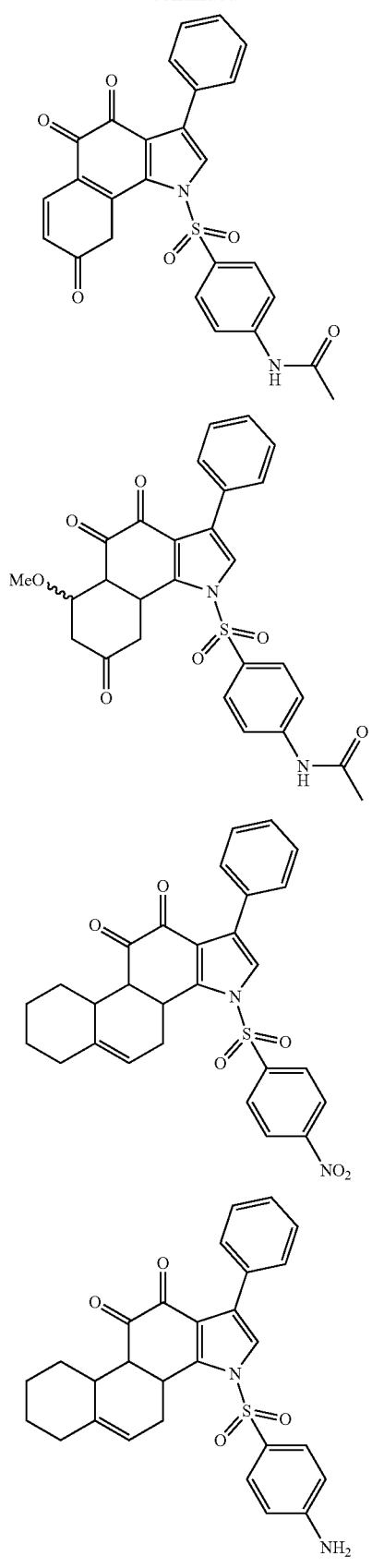
34
-continued
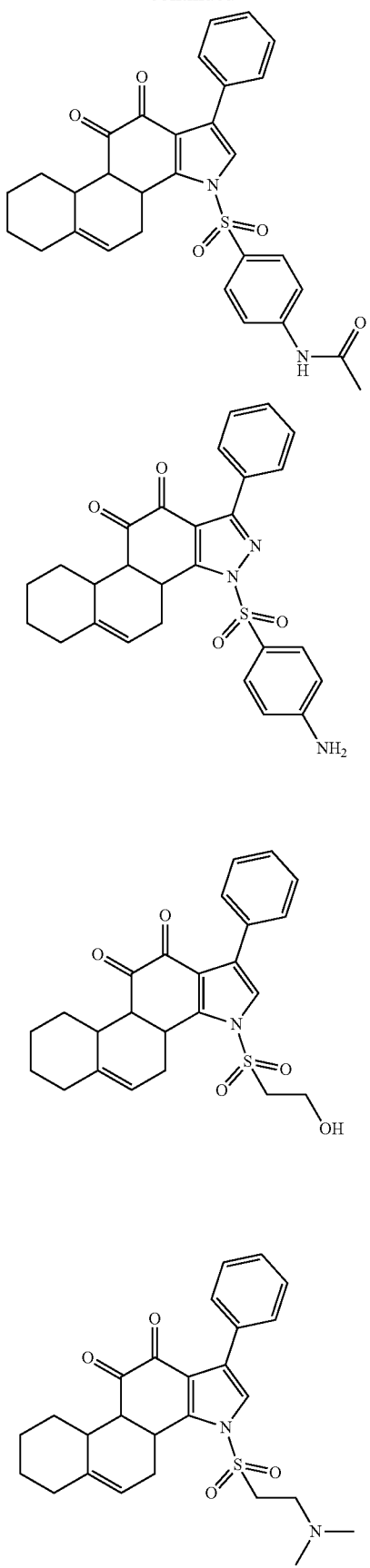

35
-continued
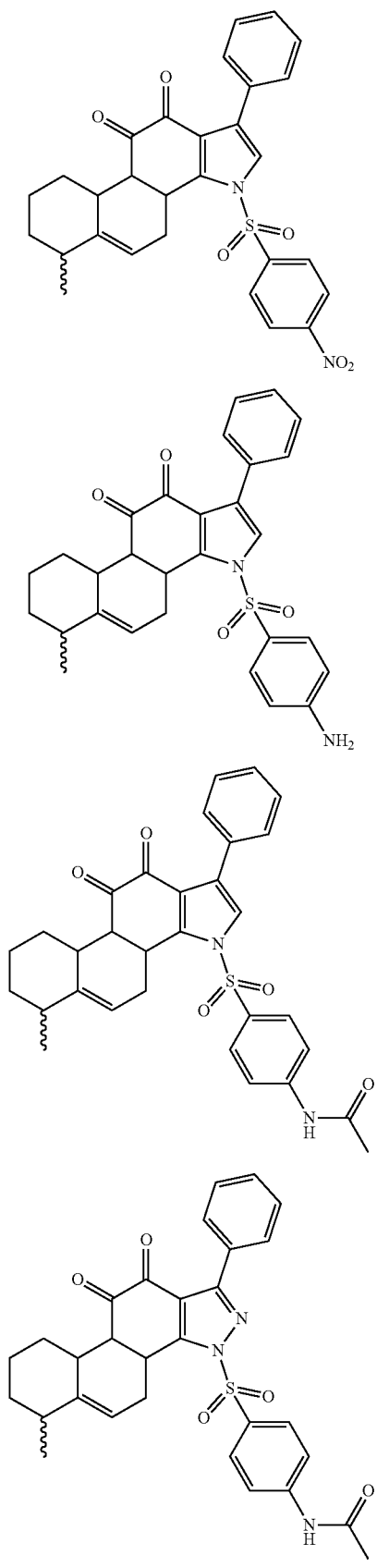
36
-continued
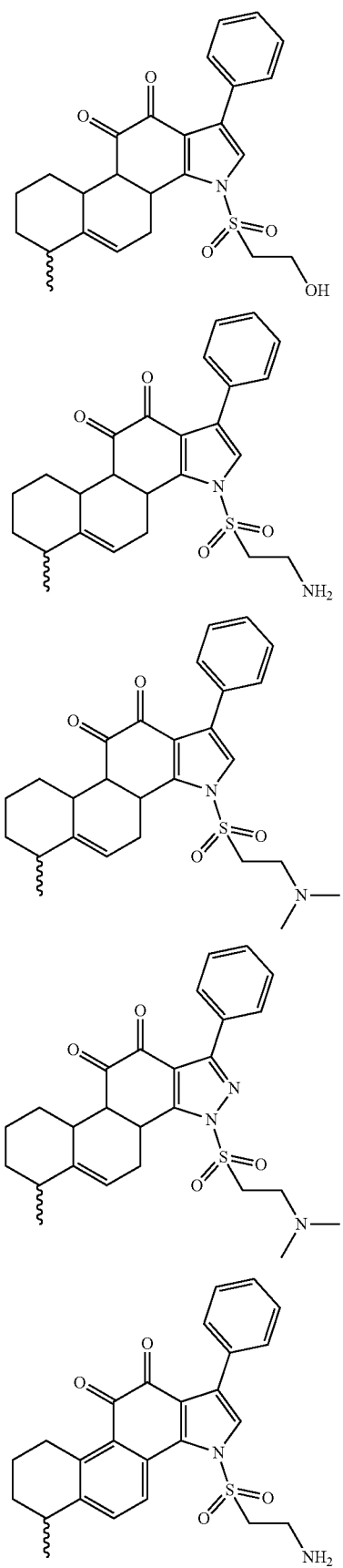

Among the compounds of formula (I) those particularly preferred include the following:

Compound 26
X is C—R5
R1 and R2 are non-substituted phenyl
R3, R4 and R5 are hydrogen
Compound 22
X is C—R5
R1 is methyl
R2 is non-substituted phenyl
R3, R4 and R5 are hydrogen
Compound 23
X is C—R5
R1 is para-NO2-phenyl
R2 is non-substituted phenyl
R3, R4 and R5 are hydrogen
Compound 24
X is C—R5
R1 is meta-NO2-phenyl
R2 is non-substituted phenyl
R3, R4 and R5 are hydrogen
Compound 25
X is C—R5
R1 is para-F-phenyl
R2 is non-substituted phenyl
R3, R4 and R5 are hydrogen
Compound 27
X is C—R5
R1 is meta-F-phenyl
R2 is non-substituted phenyl
R3, R4 and R5 are hydrogen
Compound 28
X is C—R5

R1 is non-substituted phenyl
R2 is para-MeO-phenyl
R3, R4 and R5 are hydrogen
Compound 30
X is C—R5
R1 is non-substituted phenyl
R2 is para-Me2N-phenyl
R3, R4 and R5 are hydrogen
Compound 29
X is C—R5
R1 is non-substituted phenyl
R2 is meta-MeO-phenyl
R3, R4 and R5 are hydrogen
Compound 31
X is C—R5
R1, R2 and R3 are non-substituted phenyl
R4 and R5 are hydrogen
Compound 32
X is C—R5
R1 and R2 are non-substituted phenyl
R5 is hydrogen
R3 and R4 form a bicyclo(2.2.2)oct-2-ene
Compound 33
X is C—R5
R1 and R2 are non-substituted phenyl
R5 is hydrogen
R3 and R4 form a 2-OH-naphthyl These and other particularly preferred compounds of the invention are reported in the examples.

The compounds of the invention modulate the expression of a variety of proteins associated with different diseases and can be used alone, as drugs; alternatively, they can also enhance the effects of known anti-tumor, anti-inflammatory, cardiovascular and neuroprotective agents.

In particular, the compounds of the invention can be used to modulate the expression of a variety of proteins in any disease which is characterized by an over-expression or alteration of the HuR protein and in diseases which can be prevented, ameliorated or completely treated through the modulation of mRNAs regulated by HuR and non-coding RNAs (e.g., but not limited to, cancer, inflammation, cardiovascular and neurodegenerative diseases).

Therefore, the present invention provides also compositions and methods for the "targeting" of diseases of mammals, preferably humans, characterized by an over-expression or a functional alteration of the HuR protein.

The use of the same compounds in therapy and diagnosis is a further object of the invention.

The use of the compounds of the invention in the treatment and/or prevention of diseases related to an over-expression or functional alteration of the HuR protein is a further aspect of the invention, as well as a method for the treatment and/or prevention of such diseases, which comprises administering an effective dose of at least one compound of the invention to a subject in need thereof. The subject is in this case a mammal, preferably the human being.

Examples of such proteins associated with diseases depending on HuR include CCNA2, CCNB1, CCNE1, CCND1, OSM, EIF4E, EGF, i-NOS, TSP1, MKP-1, MDM2, XIAP, SNAIL, dCK, pVHL, BRAC1, c-FMS, GATA3, GM-CSF, TM, RGS4, IL-6, IL-13, SMN, SH2D1A, NF1, PROX1, Eotaxin, PROT-alpha, CDKN1A, CDKN1B, P53, BCL2, FOXO1, CYCS, SIRT1, MCL-1, WNT5A, PLAU, PALUR, COX-2, VEGFs, PTHRP, IGF1R, MAT2A, MMP9, HIF1A, PTMA, ESR1, MSI1, DIRAS3, CCL11, FOS, MYC, P21, P27, TGF-b, IL-8, DLST, Slc25a19, DDX6, AGO2, MALAT1, PRKAA1, IFN-β, INF-γ, IL-1β, IL-2, p62, JUN, IL-4, AT-$R_1$, IL-3, IL-10, beta-adrenergic receptors, SERCA, TLR4, soluble guanylate cyclase, Glut1, CAM-1, VCAM-1, TNRC6B, miRNA-21, miRNA-16, miRNA-181s, miRNA-1192, miRNA-3134, miRNA-200c, linc-MD1, UFC1, linc-p21, H19, TDP-43, FUS and PDGF.

Preferred target proteins, which can be modulated by the compounds of the invention, are VEGFs, COX-2, TNF, IL-6, IL-17, TGF-b, TDP43, CXCR4 and INFs.

Examples of diseases that can be treated with the compounds of the invention include tumors, lymphoma, melanoma, glioma, glioblastoma, myeloma, insulinoma, hypercalcaemia, leukemia, neuroblastoma, sarcoma, polycythemia, thrombocytosis, colon cancer, lung cancer, Hodgkin's disease, macroglobulinemia; autoimmune diseases; inflammatory diseases; infections; hyperproliferative diseases; AIDS; neurodegenerative diseases and vascular diseases.

According to the present invention, tumors include the primary tumors and the metastases and can also be tumors resistant to common anti-cancer agents.

The compounds of the invention can be administered alone, in combination between them or in combination with other active ingredients, e.g. with chemotherapeutic agents, apoptosis modulators, anti-angiogenics, anti-neurodegeneratives, cardio-protectors, antivirals and anti-inflammatories.

The compounds of the invention can be administered in combination with anti-cancer agents or treatments which induce the cell death, such as for example, radiotherapy, factors relating to the TNF, kinase inhibitors, antisense molecules, antibodies, anti-estrogens; anti-androgens; chemotherapeutics for cancer; staurosporines molecules which act on cell signaling; or with modulators of the inflammatory response such as COX-2 inhibitors; anti-inflammatories; ceramides and cytokines.

The compounds of the invention can be administered in combination with antiproliferative or antineoplastic agents or treatments for example with alkylating agents, antimetabolites and products of natural origin with antitumor activity. Alkylating agents include nitrogen mustards, ethylenimines and methylamines, alkyl sulfonates, nitrosoureas and triazenes. Antimetabolites include folic acid, pyrimidine and purine derivatives. Chemotherapeutics include vinca alkaloids, epipodophyllotossine, antibiotics, enzymes, modifiers of the biological response, coordination complexes of platinum, antracendiones, methylhydrazine derivatives, adrenocortical suppressors, adrenocorticosteroids, progestinics, estrogens, androgens, anti-androgens, and analogues of the gonadotropin-releasing hormone.

Other anti-cancer agents can be however combined with the compounds of the invention.

Object of the present invention is also a combination of an effective amount of a compound of formula (I) and at least one treatment for cancer, e.g., surgery or radiotherapy.

Accordingly, the present invention further provides a method for administering a compound of formula (I) together with radiotherapy. The invention is not limited by the type, amount, or administration route used to deliver the therapeutic dose of the radiation to the subject.

The source of radiation can be internal or external to the subject. The external radiotherapy is the most common and concerns high energy radiation beam directed towards the site of the tumor through the skin by using, e.g., a linear accelerator. Internal radiotherapy concerns the positioning inside the body or close to the tumor site of a radiation emitting source, including the use of delivery systems which specifically target the tumor cells.

The animal can optionally receive radiosensitizers or radioprotectors. Radiosensitizers increase killing of tumor cells. Radioprotectors protects healthy tissues from the detrimental effect of the radiation.

Other types of radiation can be administered to the subject, as long as their dosage is tolerated without unacceptable side effects. Suitable radiotherapies include ionizing/electromagnetic radiotherapies and therapies with beams of particle radiations.

The total dose of radiation administered to the subject is preferably about 0.01 Gray (Gy) to about 100 Gy. More preferably, between about 10 Gy and about 65 Gy are administered during the course of the treatment. Whereas in some embodiments a complete radiation dose can be administered during one day, the total dose is ideally subdivided and administered during different days. Desirably, radiotherapy is administered at intervals of at least 3 days, during a period from 1 to 8 weeks. Accordingly, a daily dose of radiation will comprise about 1-5 Gy, and preferably 1-2 Gy. The daily dose of radiation should be sufficient to induce the destruction of the target cells, but break days of therapy should be included. For example, the desirable radiation is administered during 5 consecutive days, and not administered for 2 days, per each week of treatment, thus allowing 2 days of break per week. These examples of radiotherapy administration schedules are not intended, however, to limit the present invention.

In other embodiments of the present invention, a compound of formula (I) and one or more anti-cancer agents are administered to a subject under one or more of the following conditions: at different periodicities, at different durations, at different concentrations, by different administration routes, and so on. In some embodiments, the compound is administered before the therapeutic or anti-cancer agent, for example 0.5, 1, 2, 3, 4, 5, 10, 12, or 18 hours, 1, 2, 3, 4, 5, or 6 days, 1, 2, 3, or 4 weeks before the administration of the therapeutic or anti-cancer agent. In other embodiments, the compound is administered after the therapeutic or anti-cancer agent, for example 0.5, 1, 2, 3, 4, 5, 10, 12, or 18 hours, 1, 2, 3, 4, 5, or 6 days, 1, 2, 3, or 4 weeks after the administration of the therapeutic or anti-cancer agent. In some embodiments, the compound and the therapeutic or anti-cancer agent are administered at the same time but with different schedules, for example the compound is administered daily whereas the therapeutic or anti-cancer agent is administered once a week, once every two weeks, once every 3 weeks, once every four weeks. In other embodiments, the compound is administered once a week whereas the therapeutic or anti-cancer agent is administered daily, once a week, once every two weeks, once every three weeks, or once every four weeks.

Object of the invention, according to another of the aspects thereof, is pharmaceutical compositions comprising, as active ingredient, one or more compounds of formula (I) as defined above.

Said compositions preferably comprise at least one pharmaceutically acceptable carrier and can also comprise other active ingredients, for example those mentioned above.

The compositions of the invention include all the compositions where the compound of the present invention is comprised in an amount which is effective in achieving its intended aim. Although the individual needs vary, determining optimal ranges of effective amount per each component is known to persons skilled in the art. The administered dose will therefore depend on age, health and weight of the recipient, type of treatment, frequency of the treatment and nature of the desired effect.

Typically, the compound can be administered daily to mammals and in particular to humans, orally at a dose between 0.0025 and 50 mg/kg, or an equivalent amount of one of its pharmaceutically acceptable salts, of the body weight of the treated mammal. Preferably, about 0.01 to 10 mg/kg are administered orally. For the intramuscular administration, the dose is generally half of the oral dose. For example, an acceptable intramuscular dose would be about 0.0025 to about 25 mg/kg, and more preferably, about 0.01 to about 5 mg/kg. In a topical formulation, the compound can be at a concentration of about 0.01 to about 100 mg/kg per gram of carrier. In a preferred embodiment, the compound is at a concentration of about 0.07-1.0 mg/mL, more preferably about 0.1-0.5 mg/mL, still more preferably about 0.4 mg/mL. Preferably the compositions, which can be administered by oral, topical and parenteral route, are those known to the person skilled in the art, e.g., they will be in the form of: tablets, dragées, prolonged release pills and capsules, mouthwashes, gels, liquid suspension, hair dyes, hair gels, shampoos and other preparations which can be administered rectally, such as suppositories, as well as acceptable solutions for the parenteral, topical or oral administration, containing about 0.01 to 99%, preferably 0.25 to 75% of active ingredient(s).

The pharmaceutical compositions can be administered by any means to achieve the desired aim. For example, the administration can be parenteral, subcutaneous, intravenous, intramuscular, intraperitoneal, transdermal, buccal, intrathecal, intracranial, intranasal, oral or topical.

The pharmaceutical preparations of the present invention are produced as is known to one skilled in the art, e.g., by conventional mixing, granulation, sugar-coating, dissolution, or freeze-drying processes. Therefore, the pharmaceutical preparations for oral use can be obtained by combining the active ingredient with solid excipients, optionally by grinding the resulting mixture and treating the granule mixture, after adding suitable excipients, if desired and necessary, in order to obtain tables or dragée cores.

Suitable excipients are, in particular, diluents and fillers such as sugars, celluloses and calcium phosphate, as well as binders such as, e.g., starch, gelatin, cellulose and polyvinyl pyrrolidone. If desired, disaggregating agents can be added as the above mentioned starches, cross-linked polyvinyl pyrrolidone, agar and alginic acids and the salts thereof. Other useful excipients are free-flowing agents and lubricants, e.g., silica, talc, stearic acid and salts thereof and polyethylene glycol. The cores of the pills and the tablets can have suitable coating that, if desired, is resistant to digestive juices. In order to produce the coatings resistant to digestive juices, it is possible to use suitable polymers as it is well known to the person skilled of the art.

Other pharmaceutical compositions that can be used orally include hard capsules made of gelatin, as well as sealed, soft capsules made of gelatin and a plasticizer such as, e.g., glycerol or sorbitol. Hard capsules can contain the active ingredient in the form of granules which can be mixed with diluents, binders and/or lubricants and, optionally, stabilizers. In the soft capsules, the active ingredient is preferably dissolved or suspended in a suitable liquid, such as fatty oils or liquid paraffin. Moreover, stabilizers can be added.

Possible pharmaceutical compositions that can be used rectally include, e.g., suppositories, consisting of a combination of one or more active ingredients together with suitable excipients. Such suitable excipients are, e.g., natural or synthetics triglycerides, or paraffin hydrocarbons.

Formulations suitable for the parenteral administration include aqueous solutions of the active ingredient in soluble form, preferably in water. Moreover, suspensions of the active ingredients can be administered, such as suspensions of suitable injectable oils. Suitable lipophilic solvents or carriers include fatty oils or esters of synthetic fatty acids. Aqueous injections can contain substances increasing the viscosity of the suspension, such as sorbitol and dextran. Optionally, the suspension can also contain stabilizers.

The topical compositions of this invention are preferably formulated as oils, creams, lotions, unguents and the like, by choosing a suitable carrier. Suitable carriers include vegetable or mineral oils, Vaseline, fats and high molecular weight alcohols. Preferred carriers are those in which the active ingredient is soluble.

Creams are preferably formulated from a mixture of mineral oils, auto-emulsifying beeswax and water into which the active ingredient is added and dissolved in a small amount of oil. A typical example includes about 40 parts of water, about 20 parts of beeswax, about 40 parts of mineral oil and about 1 part of almond oil.

Unguents can be formulated by means of a mixture of a solution of the active ingredient into a vegetable oil with Vaseline and by letting the solution cool. A typical example of said unguent includes about 30 wt % of almond oil and about 70 wt % of Vaseline.

Lotions can be advantageously prepared by dissolving the active ingredient into a suitable high molecular weight alcohol.

In addition to be administered in pharmaceutical compositions, the compounds of formula (I) as described above can be administered as pure compounds.

Experimental Section

General Methods:

$^1$H-NMR spectra have been recorded with a Bruker Avance in $CDCl_3$, $CD_3OD$, $D_2O$, acetone-d6 or DMSO-d6 as solvent at 400 MHz or 600 MHz. $^{13}$C-NMR spectra have been recorded in $CDCl_3$, $CD_3OD$, $D_2O$, acetone-d6 or DMSO-d6 as solvent at 100 MHz or 125 MHz. The coupling constants are expressed in hertz and have been rounded to the closest 0.1 Hz. Purifications have been carried out by means of flash chromatography on silica gels (particle size 60 µm, 230-400 mesh), Kieselgel flash chromatography, or by Biotage™ [Biotage Si-12-M columns (150×12 mm; silica gel (40-63 µm), flow rate 12 ml/min; and Si-25-M columns (150×25 mm; silica gel (40-63 µm), flow rate 25 ml/min], or by means of Biotage™ $C_{18}$ inverse phase chromatography [Biotage $C_{18}$HS columns (150×12 mm; KP—$C_{18}$—HS (35-70 µm), flow rate 25 ml/min]. Final products have been purified by $C_{18}$ semi-preparative inverse phase HPLC by using an Acquas X-Terra $RP_{18}$ ODB column (19 mm×10.0 cm, 5 µm) or a Supelco Ascentis $C_{18}$ column (21.2 mm×15.0 cm, 5 µm). The solvents have been distilled and dried according to standard procedures, and the reactions requiring anhydrous conditions have been realized under nitrogen or argon atmosphere. The solvents for the reactions have been directly used from bottles unless specifically indicated. Optical rotations $[\alpha]_D^{20}$ have been measured in cells with a 1 dm pathlength and 1 mL capacity with a Perkin Elmer 241 polarimeter. LC-MS data have been acquired with an Agilent 1100 HPLC connected to an ion trap mass spectrometer Brucker Esquire 3000+ mass by means of an ES interface.

EXAMPLE 1

Synthesis of 3-(substituted Aryl) Methoxyindole N-Phenylsulfonamide (Formula IV, X=C—$R_5$; $R_1$=Phenyl; $R_2$=Substituted aryl; $R_3$-$R_5$=H; $R_6$=Me)

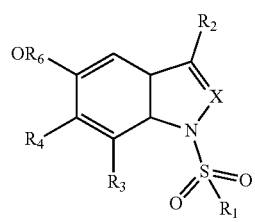

(IV)

Compounds 4, 5, referring to the structure shown above, can be prepared according to the synthesis reported in Scheme 1.

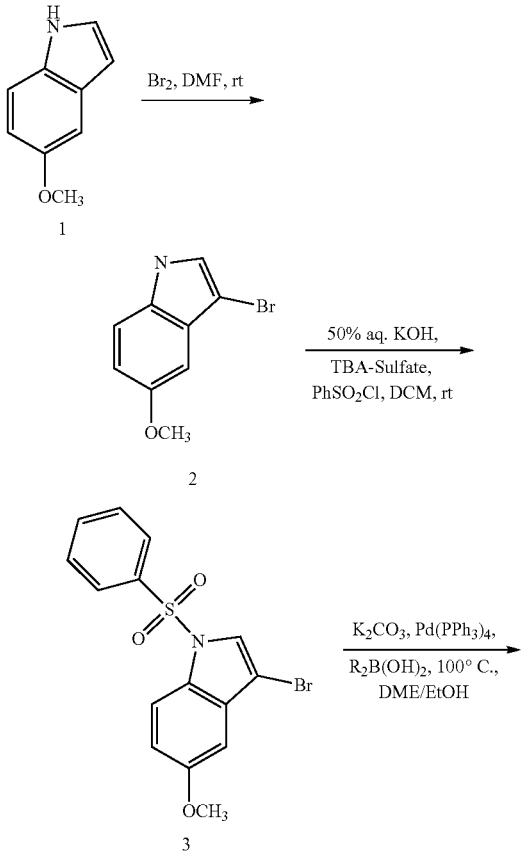

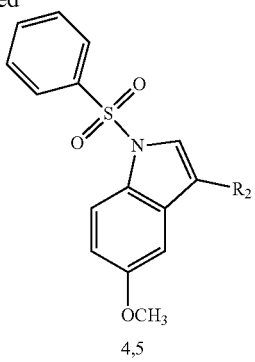

4,5

Intermediate compounds 4, 5 have been prepared by using conventional methods, comprising the following reactions:
a) Regioselective bromination of 5-methoxyindole 1 at position 3, to give compound 2;
b) Sulfonilation of indolic nitrogen at 2 under basic conditions, to give compound 3;
c) Arylation on position 3 of compound 3 by Suzuki reaction with arylboronic acids, compounds 4, 5.

Compounds 4, 5 are useful intermediate for the preparation of bicyclic aza-tanshinones.

1.1 Procedure for the Synthesis of Compound 2

A solution of $Br_2$ (0.70 mL, 13.73 mmol, 1.01 eq.) in DMF (80 mL) has been added dropwise, during few minutes, to a solution of 5-methoxy indole 1 (2 g, 13.59 mmol, 1 eq) in DMF (80 mL) at room temperature under vigorous stirring. The mixture turned orange. The reaction has been monitored by TLC (eluents: n-Hexane/EtOAc 8:2). After 19 hours, additional 0.1 equivalents of bromine (0.07 mL, 0.01 mmol) have been added. After 5 hours the reaction is complete, and the mixture is poured into an aqueous solution (≈1.6 L) containing ammonia (0.5%) and $Na_2S_2O_3 \cdot 5H_2O$ (0.1%) [1.6 L $H_2O$, 28.53 mL $NH_3$, 2.48 g $Na_2S_2O_3$, $5H_2O$]. The formed brownish precipitate has been filtered on a Buchner funnel and washed with cold water (4×100 mL). The solid has been dried overnight in the crystallization vessel. Pure 3-bromo-5-methoxyindole 2 has been obtained as brownish amorphous solid.

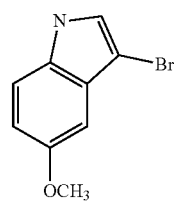

2. Yield: 74% (2.28 g, MW 226.07, 10.08 mmol). Analytical characterization: $^1$H-NMR (400 MHz, acetone-d6): δ: 10.41 (bs, 1H), 7.40 (d, 1H), 7.35 (d, J=8.8 Hz, 1H), 6.93 (d, J=2.4 Hz, 1H), 6.84 (dd, J=8.8, 2.4 Hz, 1H), 3.84, (s, 3H).

1.2 Procedure for the Synthesis of Compound 3

A 50% KOH aqueous solution (4.80 mL, 8 eq.) has been added under stirring to a mixture of 3-bromo-5-methoxyindole 2 (1.15 g, 5.09 mmol, 1 eq) and n-$Bu_4N^+HSO_4^-$ (173 mg, 0.51 mmol, 0.1 eq) in DCM (26 mL). The reaction has been vigorously stirred at room temperature for 10 minutes. Then, a solution of benzenesulfonyl chloride (1.10 mL, 8.65 mmol, 1.7 eq) in DCM (26 mL) has been added. The mixture turned orange-brown. The reaction has been monitored by TLC (eluents: n-Hexane/EtOAc 9:1). After 3 hours the reaction has been stopped by diluting with 60 mL of distilled water and extracted with DCM (2×100 mL). The pooled organic phases have been washed with water (2×100 mL) and brine (2×100 mL) and dried over sodium sulfate. The solvent has been evaporated under reduced pressure, providing 2.41 g of brownish crude solid. The crude has been purified by means of three crystallizations from n-Hexane/DCM 1/0.8. The pure 1-phenylsulfonyl-3-bromo-5-methoxyindole 3 has been obtained as white crystalline solid.

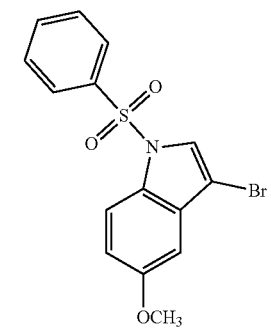

3. Yield: 90% (1.67 g, MW 366.23, 4.56 mmol). Analytical characterization: $^1$H-NMR (400 MHz, acetone-d6): δ: 8.04-8.01 (m, 2H), 7.96 (d, J=9.1 Hz, 1H), 7.87 (s, 1H), 7.72-7.68 (tt, J=7.5, 1.2, 1H), 7.62-7.58 (m, 2H), 7.05 (dd, J=9.1, 2.5 Hz, 1H), 6.94 (d, J=2.5 Hz, 1H), 3.85 (s, 3H).

1.3 General Procedure for the Synthesis of Compounds 4, 5

1-phenylsulfonyl-3-bromo-5-methoxyindole 3 (1 eq) and alkyl boronic acid (1.17 eq) have been added to a two-neck round bottom flask provided with a gas valve on the lateral neck, and the flask has been left under nitrogen flow to remove any traces of oxygen. The central neck has been closed with a rubber septum, then anhydrous DME (until reaching the final concentration of 0.056M for 3) and a previously degassed 2 M aqueous solution of $K_2CO_3$ (1.29 eq) have been added under stirring. Finally, Pd Tetrakis (0.05 eq) and previously degassed EtOH (a quarter with respect to DME, until reaching the final concentration of 0.056M for 3) have been added. While stirring the resulting yellow solution under nitrogen flow, the rubber septum has been removed and a condenser and a gas valve have been installed on the central neck. The pale yellow solution has been heated under reflux for 8 hours at ≈100° C., under stirring and nitrogen atmosphere and then stirred at room temperature overnight. The reaction has been then diluted with a saturated solution of $NH_4Cl$ and extracted with EtOAc (3 times). The pooled organic phases have been washed with a saturated solution of $NH_4Cl$ and brine, then dried over $Na_2SO_4$ and filtered. The resultant crude has been purified by flash chromatography on silica gel (eluents: n-Hexane/EtOAc). The 1-phenylsulfonyl-3-aryl-5-methoxyindoles 4, 5 have been obtained as amorphous solids. 1-phenylsulfonyl-3-phenyl- 5-methoxyindole 4 has been synthesized by means of the general procedure described above, starting from compound 3 (538 mg, 1.47 mmol) and by purifying the yellow crude oil (715 mg) with n-Hexane/EtOAc 9/1 as eluting mixture.

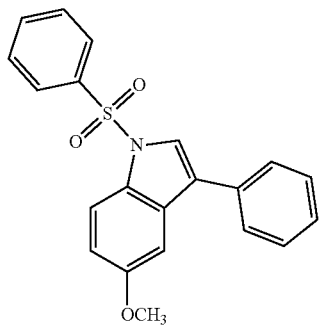

4

4. Yield: 92% (white solid, 490 mg, MW 363.43, 0.27 mmol). Analytical characterization: $^1$H-NMR (400 MHz, acetone-d6): δ: 8.08-8.06 (m, 2H), 8.02 (d, J=9.1 Hz, 1H), 7.89 (s, 1H), 7.73-7.67 (m, 3H), 7.62-7.58 (m, 2H), 7.53-7.49 (m, 2H), 7.43-7.39 (m, 1H), 7.28 (d, J=2.5 Hz, 1H), 7.05 (dd, J=9.1, 2.5 Hz, 1H), 3.83 (s, 3H).

1-phenylsulfonyl-3-(4-N,N-dimethylaminophenyl)-5-methoxyindole 5 has been synthesized by means of the general procedure described above, starting from compound 3 (100 mg, 0.27 mmol) and by purifying the yellow crude oil (124 mg) with n-Hexane/EtOAc 8/2 as eluting mixture.

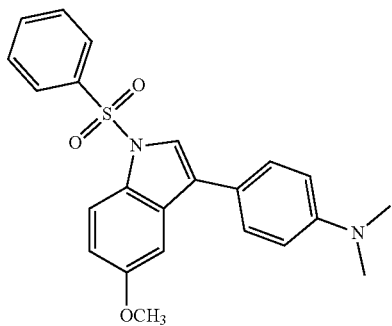

5

5. Yield: 83% (yellow solid, 91 mg, MW 406.1, 0.22 mmol). Analytical characterization: $^1$H-NMR (400 MHz, acetone-d6): δ: 8.05-8.02 (m, 2H), 7.99 (d, J=9.4 Hz, 1H), 7.71 (s, 1H), 7.68-7.64 (m, 1H), 7.60-7.57 (m, 2H), 7.53 (d, J=8.6 Hz, 2H), 7.25 (d, J=2.5 Hz, 1H), 7.01 (dd, J=2.5, 9.4 Hz, 1H), 6.86 (d, J=8.6 Hz, 2H), 3.83 (s, 3H), 3.01 (s, 6H). $^{13}$C-NMR (75.4 MHz, acetone-d6): δ: 157.0, 150.3, 137.8, 134.1, 131.0, 130.3, 129.5, 128.4, 126.8, 124.8, 122.5, 120.6, 114.7, 113.7, 112.7, 103.0, 55.0, 39.6.

EXAMPLE 2

Synthesis of 3-Methoxyphenyl Hydroxyindole N-Phenylsulfonamides (Formula IV, X═C—R$_5$; R$_1$=Phenyl; R$_2$=m,p-OMePhenyl; R$_3$-R$_6$═H)

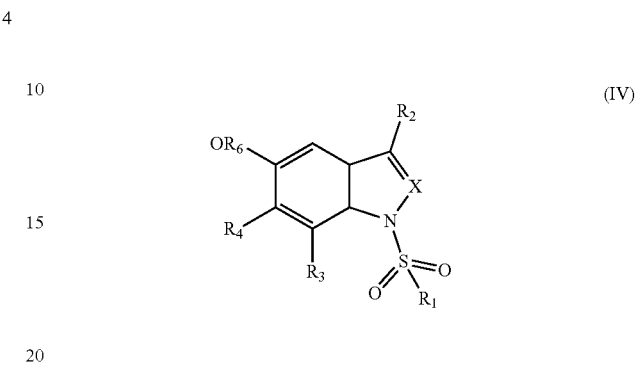

Some of the compounds referring to the structure shown above can be prepared according to a synthesis reported in Scheme 2, comprising the following conventional reactions:

a) Demethylation of methoxyl group from methoxyindole compound 3 under highly acidic conditions, to give compound 6;
b) Arylation at position 3 of compound 6 by means of a Suzuki reaction with methoxyphenylboronic acids, to give compounds 7, 8.

Scheme 2

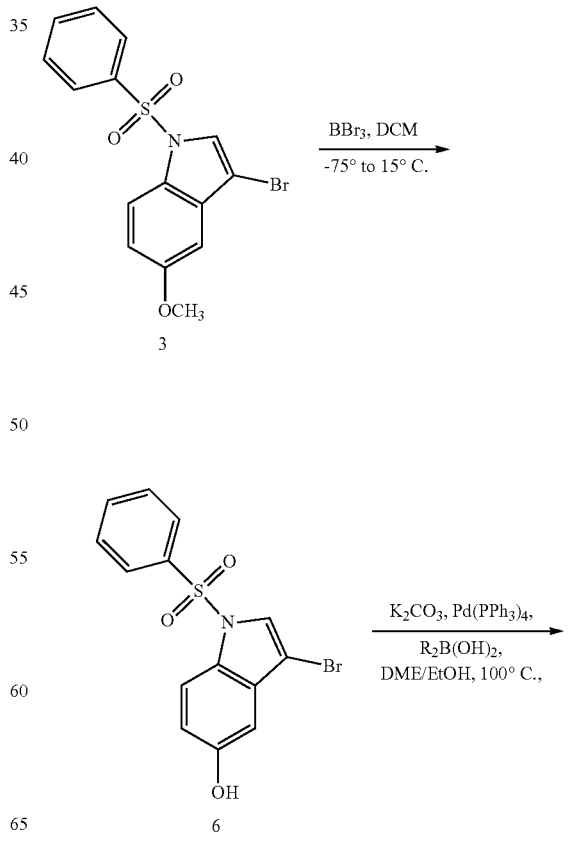

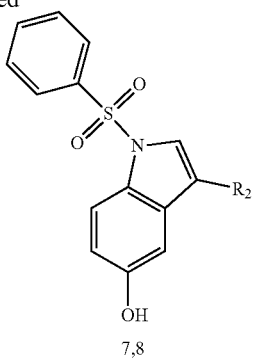

7,8

2.1 Procedure for the Synthesis of Compound 6

A 1 M solution of BBr$_3$ (1.75 mL, 1.75 mmol, 6 eq) in DCM has been slowly added under stirring to a solution of 1-phenylsulfonyl-3-bromo-5-methoxyindole 3 (105 mg, 0.29 mmol, 1 eq) in anhydrous DCM (final concentration 0.2 M in 3), under nitrogen and at −78° C. The temperature has been slowly raised up to room temperature by monitoring the reaction by TLC. The resulting solution has been immediately diluted with water (one sixth in volume with respect to DCM) and neutralized with a saturated solution of NaHCO$_3$. The aqueous phase has been extracted with DCM (5 mL×3) and the pooled organic phases have been then washed with brine, dried over Na$_2$SO$_4$, and filtered. The solvent has been removed under reduced pressure. The crude has been purified by flash chromatography on silica gel (eluents: n-Hexane/EtOAc 9/1). The pure 1-phenylsulfonyl-3-bromo-5-hydroxyindole 6 has been obtained as yellow amorphous solid.

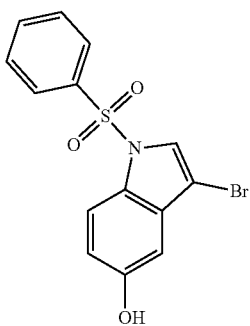

6

6. Yield: 75% (74 g, MW 352.20, 0.21 mmol). Analytical characterization: $^1$H-NMR (400 MHz, acetone-d6): δ: 8.56 (s, 1H), 8.04-8.01 (m, 2H), 7.91 (d, J=8.9 Hz, 1H), 7.84 (s, 1H), 7.73-7.67 (m, 1H), 7.63-7.58 (m, 2H), 7.00 (dd, J=8.9, 2.6 Hz, 1H), 6.88 (d, J=2.6 Hz, 1H). $^{13}$C NMR (75.4 MHz, acetone-d6): δ: 155.9, 138.5, 136.1, 132.5, 131.1, 129.8, 128.3, 127.7, 116.7, 116.3, 105.8, 100.8. ESI-MS: m/z 352.1 [M+H]$^+$; calculated mass for C$_{14}$H$_{10}$BrNO$_3$S: 351.0.

2.2 General Procedure for the Synthesis of Compounds 7, 8

To a two-neck round bottom flask provided with a calcium chloride valve on the lateral neck, 1-phenylsulfonyl-3-bromo-5-hydroxy indole 6 (1 eq) and a methoxyphenylboronic acid (1.17 eq) have been added, and the flask has been left under nitrogen flow to remove any traces of oxygen. The central neck has been sealed with a rubber septum, then anhydrous DME (until reaching the final concentration of 0.056M for 6) and a previously degassed 2 M aqueous solution of K$_2$CO$_3$ (1.29 eq) have been added under stirring. Finally, Pd Tetrakis (0.05 eq) and previously degassed EtOH (a quarter with respect to DME, until the final concentration of 0.056 M for 3) have been added. During stirring of the resulting pale yellow solution, under nitrogen flow, the rubber septum has been removed, then a condenser and a calcium chloride valve have been installed on the central neck. The pale yellow solution has been heated under reflux, under stirring and nitrogen atmosphere for 8 hours at ≈100° C., and then stirred at room temperature overnight. The reaction has been then diluted with a saturated solution of NH$_4$Cl and extracted with EtOAc (3 times). The pooled organic phases have been washed with a saturated solution of NH$_4$Cl and with brine, then dried over Na$_2$SO$_4$ and filtered. The resultant crude has been purified by flash chromatography on silica gel (eluents: n-Hexane/EtOAc). The 1-phenylsulfonyl-3-methoxyphenyl-5-hydroxyindoles 7, 8 have been obtained as amorphous solids. 1-phenylsulfonyl-3-(p-methoxyphenyl)-5-hydroxyindole 7 has been synthesized by means of the general procedure described above, starting from compound 6 (100 mg, 0.28 mmol) and by purifying the green crude solid (148 mg) with n-Hexane/EtOAc 7/3 as eluting mixture.

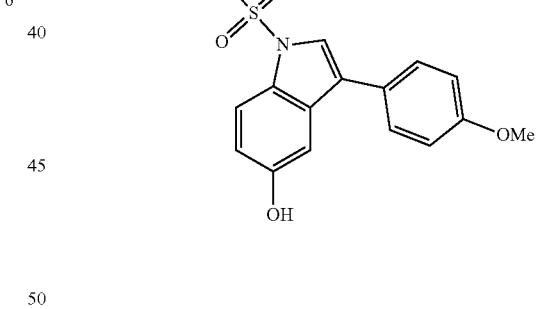

7

7. Yield: 87% (white solid, 94 mg, MW 379.43, 0.25 mmol). Analytical characterization: $^1$H-NMR (400 MHz, acetone-d6): δ: 8.28 (bs, 1H), 8.05-8.03 (m, 2H), 7.93 (d, J=8.8 Hz, 1H), 7.76 (s, 1H), 7.67-7.61 (m, 1H), 7.61-7.57 (m, 4H), 7.19 (d, J=2.0 Hz, 1H), 7.08-7.05 (m, 2H), 6.96 (dd, J=8.8, 2.0 Hz, 1H), 3.87 (s, 3H). $^{13}$C-NMR (75.4 MHz, acetone-d6): δ: 157.0, 150.3, 137.8, 134.1, 131.0, 130.3, 129.5, 128.4, 126.8, 124.8, 122.5, 120.6, 114.7, 113.7, 112.7, 103.0, 55.0, 39.6. ESI-MS: m/z 380.3 [M+H]$^+$; calculated mass for C$_{21}$H$_{17}$NO$_4$S: 379.1.

1-phenylsulfonyl-3-(m-methoxyphenyl)-5-hydroxyindole 8 has been synthesized by means of the general procedure described above, starting from compound 6 (150 mg, 0.43 mmol) and by purifying the yellow crude solid (215 mg) with n-Hexane/EtOAc 7/3 as eluting mixture.

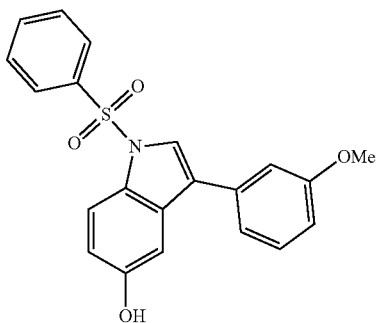

8

8. Yield: 79% (white solid, 129 mg, MW 379.43, 0.34 mmol). Analytical characterization: $^1$H-NMR (400 MHz, acetone-d6): δ: 8.33 (s, 1H), 8.09-8.03 (m, 2H), 7.95 (d, J=8.4 Hz, 1H), 7.88 (s, 1H), 7.72-7.66 (m, 1H), 7.63-7.56 (m, 2H), 7.41 (t, J=7.8 Hz, 1H), 7.27-7.20 (m, 3H), 7.00-6.94 (m, 2H), 3.89 (s, 3H). $^{13}$C-NMR (75.4 MHz, acetone-d6): δ: 165.4, 159.7, 143.1, 139.7, 139.4, 135.7, 135.1, 134.7, 129.4, 129.0, 125.1, 119.9, 119.3, 118.4, 118.2, 110.3, 59.9. ESI-MS: m/z 781.0 [2M+Na]$^+$; calculated mass for $C_{21}H_{17}NO_4S$: 379.1.

EXAMPLE 3

Synthesis of 3-Phenyl Indole N-Alkyl/arylsulfonamides (Formula IV, X=C—R$_5$; R$_1$=Substituted Alkyls, Aryls; R$_2$=Phenyl; R$_3$-R$_5$=H; R$_6$=Me)

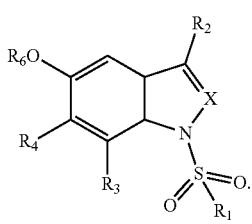

Some of the compounds referring to the structure shown above can be prepared according to a synthesis reported in Scheme 3, comprising the following conventional reactions:

a) Removal of the phenylsulfonamide group of compound 4 under aqueous basic conditions, to give compound 9;
b) Introduction of suitable alkyl- or aryl-sulfonamides on the indolic nitrogen of compound 9, to give compounds 10-14.

Scheme 3

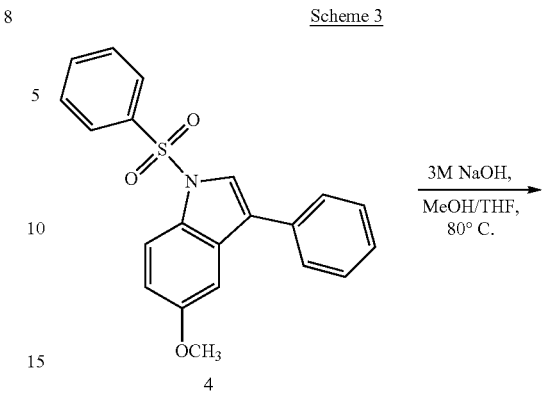

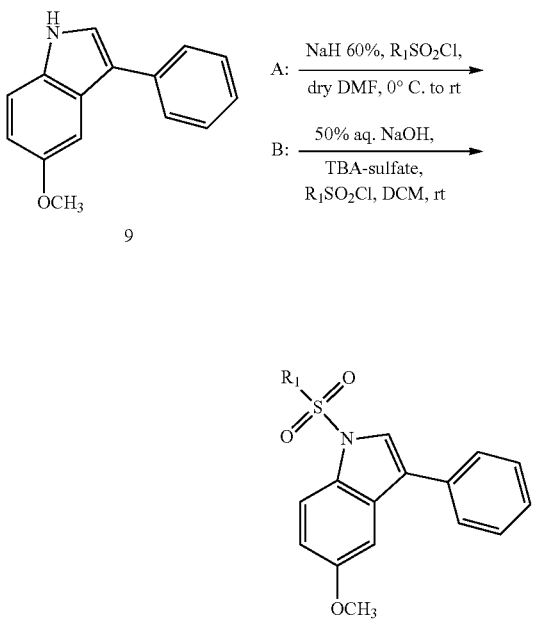

3.1 Procedure for the Synthesis of Compound 9

A 3 M NaOH solution (21 mL, 63.29 mmol, 46 eq.) has been added dropwise to a solution of 5-methoxy-3-phenyl-1-phenylsulfonylindole 4 (500 mg, 1.38 mmol, 1 eq) in MeOH/THF 2/1 (200 mL). The resulting pink mixture has been heated up to 80° C. The reaction has been monitored by TLC (eluents: n-Hexane/EtOAc 8:2). After 2 h the reaction has been stopped by acidification with 3 N HCl (23 mL), and the organic solvent has been evaporated under reduced pressure. The aqueous residue has been extracted with EtOAc (3×100 mL). The pooled organic phases have been washed with brine (450 mL) and dried over sodium sulfate. The solvent has been evaporated under reduced pressure, providing 365 mg of crude as brown oil. This has been purified by flash chromatography on silica gel by using n-Hexane/EtOAc 85:15 as eluents. The pure 3-phenyl-5-methoxyindole 9 has been obtained as white crystalline solid.

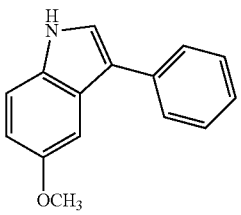

9

9. Yield 98% (301 mg, MW 223.27, 1.35 mmol). Analytical characterization: $^1$H-NMR (400 MHz, acetone-d6): δ: 10.33 (bs, 1H), 7.72-7.69 (m, 2H), 7.58 (d, J=2.6 Hz, 1H), 7.47-7.36 (m, 4H), 7.26-7.21 (m, 1H), 6.85 (dd, J=8.8, 2.6 Hz, 1H), 3.84 (s, 3H).

3.2 Procedure A for the Synthesis of Compound 10

A solution of 3-phenyl-5-methoxy indole 9 (38 mg, 0.17 mmol, 1 eq) in anhydrous DMF (1 mL) has been slowly added under stirring to a suspension of 60% NaH (1.2 eq) in anhydrous DMF (1 mL), under nitrogen and at 0° C. The reaction has been vigorously stirred at 0° C. for 30 minutes. Then a solution of $CH_3SO_2C_1$ (1.2 eq) in DMF (200 μL) has been added, and the formation of a white precipitate has been observed. After stirring for 10 minutes at 0° C. the temperature has been slowly raised up to room temperature. The reaction has been monitored by TLC (eluents: n-Hexane/EtOAc 8:2). When the reaction is completed, the solution has been diluted with distilled water (20 mL) and extracted with diethyl ether (3×20 mL). The pooled organic phases have been sequentially washed with saturated solutions of $NaHCO_3$ (3×20 mL), water (30 mL) and brine (30 mL), and dried over sodium sulfate. The solvent has been evaporated under reduced pressure, providing a brown crude oil (45 mg) then purified by flash chromatography on silica gel (eluting mixtures: n-Hexane/EtOAc). The pure 1-methylsulfonyl-3-phenyl-5-methoxyindole 10 has been obtained as yellow amorphous solid.

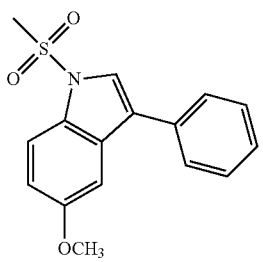

10

10. Yield 62% (yellow oil, 32 mg, MW 301.36, 0.11 mmol). Analytical characterization: $^1$H-NMR (400 MHz, acetone-d6): δ: 7.89 (d, J=9.1 Hz, 1H), 7.77-7.74 (m, 2H), 7.66 (s, 1H), 7.55-7.49 (m, 2H), 7.43-7.38 (m, 2H), 7.08 (dd, J=9.1, 2.3 Hz, 2H), 3.88 (s, 3H), 3.35 (s, 3H).

3.3 General Procedure B for the Synthesis of Compounds 11-14

A 50% KOH aqueous solution (8 eq.) has been added under vigorous stirring to a mixture of 3-phenyl-5-methoxy indole 9 (1 eq) and n-Bu$_4$N$^+$HSO$_4^-$ (0.1 eq) in DCM (concentration of 0.2 M in 9). The reaction has been vigorously stirred at room temperature for 10 minutes. Then, a solution of arylsulfonylchloride (1.7 eq) in DCM (total concentration of 0.1M in 9) has been added. The reaction has been monitored by TLC (eluent mixtures: n-Hexane/EtOAc). When the reaction is completed, it his has been diluted with distilled water (same as DMC), separated and the aqueous phase has been extracted with DCM (same volume as water, 2 times). The pooled organic phases have been washed with water (same as DCM) and brine (same as DCM) and dried over sodium sulfate. The solvent has been evaporated under reduced pressure, providing the crude product. The crude has been purified by flash chromatography on silica gel (eluting mixtures: n-Hexane/EtOAc). The pure 1-arylsulfonyl-3-phenyl-5-methoxyindoles 11-14 have been obtained as amorphous solids. 1-(p-Nitrophenylsulfonyl)-3-phenyl-5-methoxyindole 11 has been synthesized by means of the General procedure B described above, starting from compound 9 (100 mg, 0.45 mmol) and by purifying the orange crude solid (226 mg) with n-Hexane/EtOAc 8/2 as eluting mixture.

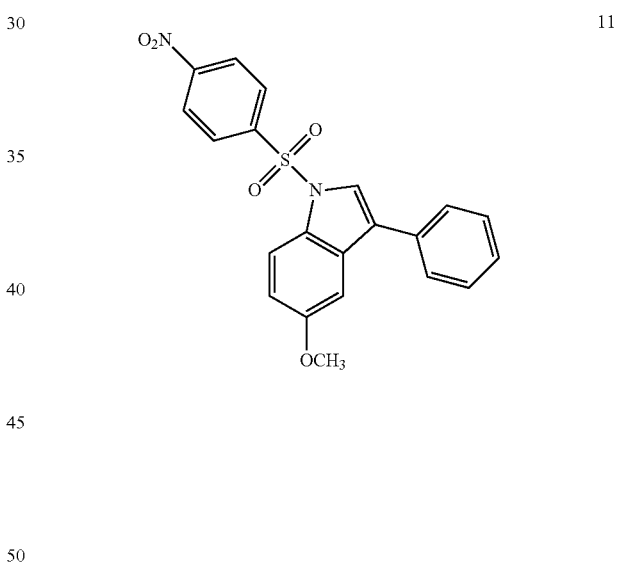

11

11. Yield 86% (yellow solid, 158 mg, MW 408.1, 0.39 mmol). Analytical characterization: $^1$H-NMR (400 MHz, acetone-d6): δ: 8.45-8.33 (m, 4H), 8.04 (d, J=9.5 Hz, 1H), 7.93 (s, 1H), 7.76-7.70 (m, 2H), 7.55-7.48 (m, 2H), 7.46-7.38 (m, 1H), 7.30 (d, J=2.9 Hz, 1H), 7.07 (dd, J=9.5, 2.9 Hz, 1H), 3.85 (s, 3H); $^{13}$C-NMR (100 MHz, acetone-d6): δ: 158.3, 151.9, 143.4, 133.4, 131.4, 130.7, 129.8, 129.4, 128.7, 126.0, 125.7, 125.0, 115.6, 115.2, 104.0, 55.9. ESI-MS: m/z 409.2 [M+H]$^+$; calculated mass for $C_{21}H_{16}N_2O_5S$: 408.1.

1-(m-Nitrophenylsulfonyl)-3-phenyl-5-methoxyindole 12 has been synthesized by means of the General procedure B described above, starting from compound 9 (200 mg, 0.90 mmol) and by purifying the yellow crude oil (472 mg) with n-Hexane/EtOAc 85/15 as eluting mixture.

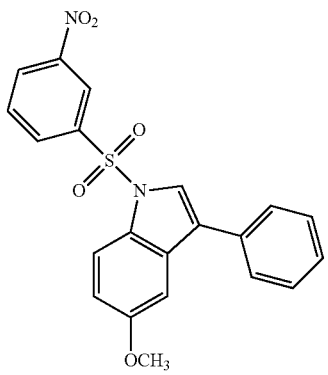

12

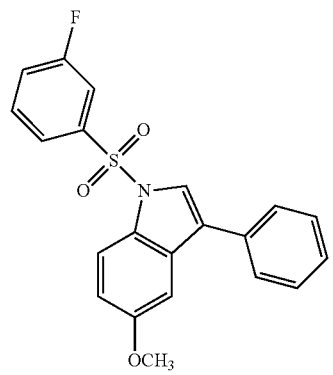

14

12. Yield 88% (yellow solid, 324 mg, MW 408.1, 0.79 mmol). Analytical characterization: $^1$H-NMR (400 MHz, acetone-d6): δ: 8.79-8.78 (m, 1H), 8.54-8.48 (m, 2H), 8.07 (d, J=9.1 Hz, 1H), 7.96 (s, 1H), 7.94-7.92 (m, 1H), 7.73-7.71 (m, 2H), 7.53-7.49 (m, 2H), 7.44-7.42 (m, 1H), 7.30 (d, J=2.6 Hz, 1H), 7.10 (dd, J=9.1, 2.6 Hz, 1H), 3.84 (s, 3H); $^{13}$C-NMR (100 MHz, acetone-d6): δ: 162.6, 153.7, 144.3, 137.7, 136.7, 135.8, 135.3, 134.1, 134.0, 133.0, 130.1, 129.2, 126.9, 119.9, 119.5, 108.4, 60.3. ESI-MS: m/z 409.1 [M+H]$^+$; calculated mass for $C_{21}H_{16}N_2O_5S$: 408.1.

1-(p-Fluorophenylsulfonyl)-3-phenyl-5-methoxyindole 13 has been synthesized by means of the General procedure B described above, starting from compound 9 (100 mg, 0.45 mmol) and by purifying the yellow crude solid (232 mg) with n-Hexane/EtOAc 9/1 as eluting mixture.

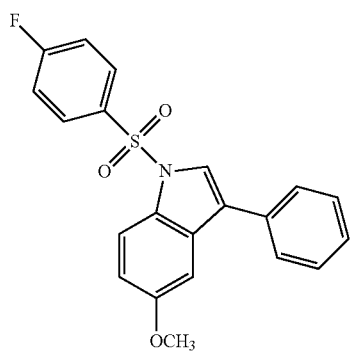

13

13. Yield 90% (white solid, 154 mg, MW 381.1, 0.40 mmol). Analytical characterization: $^1$H-NMR (400 MHz, acetone-d6): δ: 8.18-8.14 (m, 2H), 8.01 (d, J=9.3 Hz, 1H), 7.88 (s, 1H), 7.73-7.70 (m, 2H), 7.53-7.48 (m, 2H), 7.43-7.32 (m, 3H), 7.29 (d, J=2.7 Hz, 1H), 7.05 (dd, J=9.3, 2.7 Hz, 1H), 3.84 (s, 3H); $^{13}$C-NMR (100 MHz, acetone-d6): δ: 172.7, 169.4, 162.5, 139.4, 138.0, 135.4, 134.1, 132.9, 132.8, 129.6, 129.2, 122.0, 119.9, 119.3, 108.1, 60.2. ESI-MS: m/z 785.0 [2M+Na]$^+$; calculated mass for $C_{21}H_{16}FNO_3S$: 381.1.

1-(m-Fluorophenylsulfonyl)-3-phenyl-5-methoxyindole 14 has been synthesized by means of the General procedure B described above, starting from compound 9 (200 mg, 0.90 mmol) and by purifying the yellow crude oil (615 mg) with n-Hexane/EtOAc 9/1 as eluting mixture.

14. Yield 92% (white solid, 315 mg, MW 381.1, 0.83 mmol). Analytical characterization: $^1$H-NMR (400 MHz, acetone-d6): δ: 8.03 (d, J=8.9 Hz, 1H), 7.94-7.93 (m, 1H), 7.92 (s, 1H), 7.86 (dd, J=8.2, 1.8 Hz, 1H), 7.74-7.72 (m, 2H), 7.67 (ddd, J=7.6, 4.5 Hz, 1H), 7.53-7.50 (m, 2H), 7.47-7.46 (m, 1H), 7.43-7.40 (m, 1H), 7.29 (d, J=2.6 Hz, 1H), 7.06 (dd, J=8.9, 2.6 Hz, 1H), 3.84 (s, 3H); $^{13}$C-NMR (100 MHz, acetone-d6): δ: 162.0, 161.4, 140.4, 133.7, 132.8, 131.2, 130.8, 129.8, 128.6, 128.5, 125.4, 125.0, 124.0, 122.2, 115.6, 115.0, 114.7, 103.7, 56.0. ESI-MS: m/z 382.1 [M+H]$^+$; calculated mass for $C_{21}H_{16}FNO_3S$: 381.1.

EXAMPLE 4

Synthesis of 1-Alkyl/arylsulfonyl-3-Aryl-4,5-dioxo indoles (Formula I, X=C—R$_5$; R$_1$=Substituted Alkyls, Aryls; R$_2$=Aryls; R$_3$-R$_5$=H)

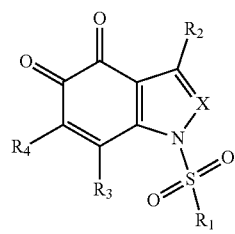

(I)

Some of the compounds referring to the structure shown above can be prepared from the already described intermediates (examples 1-3) according to a synthesis reported in Scheme 4, comprising the following steps:

a) Removing the methyl group from methoxyindole compounds 4, 5, 10-14 under highly acidic conditions, to give compounds 15-21;

b) Oxidizing the hydroxyindole compounds 7, 8, 15-21/ synthesis of ortho quinone, to give the bicyclic aza-tanshinones 22-30.

Scheme 4

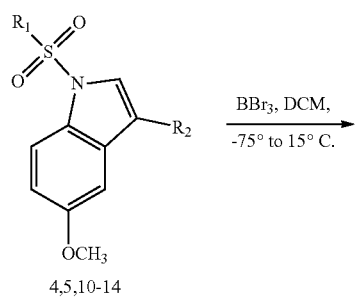

4,5,10-14

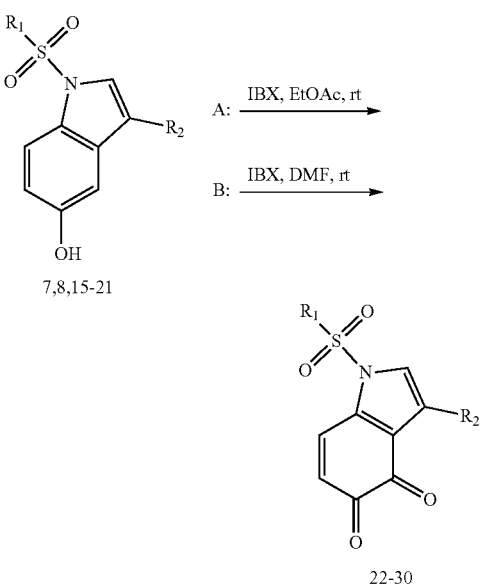

4.1 General Procedure for the Synthesis of Hydroxy Indoles 15-21

A 1 M solution of BBr$_3$ (6 eq) in DCM has been slowly added under stirring to a solution of 5-methoxyindoles (1 eq) in anhydrous DCM (0.2 M final concentration of methoxy-indoles), under nitrogen at −78° C. The temperature has been slowly raised up to room temperature by monitoring the reaction by TLC. The resulting solution has been immediately diluted with water (one sixth in volume with respect to DCM) and neutralized with a saturated solution of NaHCO$_3$. The aqueous phase has been extracted with DCM (same volume as water, 3 times), and the pooled organic phases have been washed with brine (one third of the DCM total volume), dried over sodium sulfate and filtered. The solvent has been removed under reduced pressure. The crude has been purified by flash chromatography on silica gel (eluents: n-Hexane/EtOAc). The pure hydroxyindoles 15-21 have been obtained as solids of various color.

1-Phenylsulfonyl-3-phenyl-5-hydroxyindole 15 has been synthesized by means of the general procedure described above, starting from compound 4 (160 mg, 0.44 mmol) and by purifying the yellow crude solid (170 mg) with n-Hexane/EtOAc 8/2 as eluting mixture.

15. Yield: 87% (white solid, 134 mg, MW 349.4, 0.38 mmol). Analytical characterization: $^1$H-NMR (400 MHz, acetone-d6): δ: 8.29 (s, 1H), 8.05-8.03 (m, 2H), 7.93 (d, J=8.9 Hz, 1H), 7.84 (s, 1H), 7.69-7.65 (m, 3H), 7.60-7.56 (m, 2H), 7.50-7.46 (m, 2H), 7.38 (tt, J=7.4, 1.2 Hz, 1H), 7.21 (d, J=2.4 Hz, 1H), 6.96 (dd, J=8.9, 2.4 Hz, 1H). $^{13}$C NMR (75.4 MHz, acetone-d6): δ: 155.5, 138.9, 135.1, 134.0, 131.4, 130.4, 129.8, 128.6, 128.4, 127.8, 124.9, 115.6, 115.0, 106.0. ESI-MS: m/z 721.0 [2M+Na]$^+$; calculated mass for C$_{20}$H$_{15}$NO$_3$S: 349.5.

1-Methylsulfonyl-3-phenyl-5-hydroxyindole 16 has been synthesized by means of the general procedure described above, starting from compound 10 (29 mg, 0.10 mmol) and obtaining a blue crude solid (26 mg) which has been considered pure enough.

16. Yield: 91% (blue solid, 2 mg, MW 287.3, 0.09 mmol). Analytical characterization: $^1$H-NMR (400 MHz, acetone-d6): δ: 8.34 (bs, 1H), 7.95 (d, J=8.9 Hz, 1H), 7.86-7.84 (m, 2H), 7.77 (s, 1H), 7.68-7.63 (m, 2H), 7.56-7.51 (m, 1H), 7.46 (d, J=2.1 Hz, 1H), 7.14 (dd, J=8.9, 2.1 Hz, 1H), 3.46 (s, 3H).

1-(p-Nitrophenylsulfonyl)-3-phenyl-5-hydroxyindole 17 has been synthesized by means of the general procedure described above, starting from compound 11 (158 mg, 0.39 mmol) and by purifying the yellow crude solid (183 mg) with n-Hexane/EtOAc 75/25 as eluting mixture.

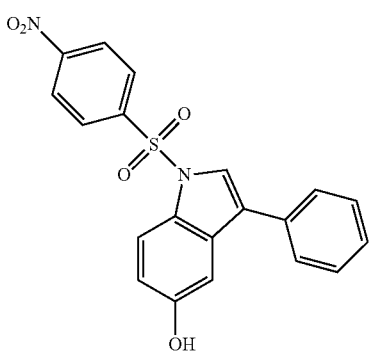

17

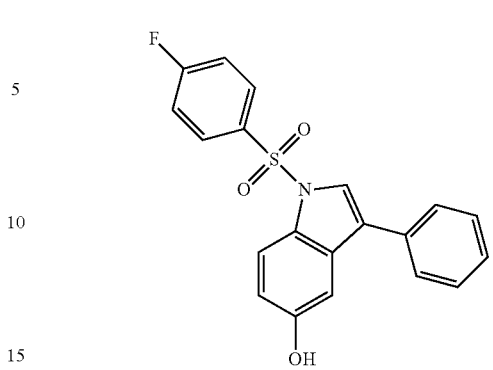

19

17. Yield: 79% (yellow solid, 120 mg, MW 394.4, 0.30 mmol). Analytical characterization: $^1$H-NMR (400 MHz, acetone-d6): δ: 8.42-8.32 (m, 4H), 7.95 (d, J=8.9 Hz, 1H), 7.88 (s, 1H), 7.69-7.66 (m, 2H), 7.53-7.47 (m, 2H), 7.43-7.36 (m, 1H), 7.22 (d, J=2.7 Hz, 1H), 6.99 (dd, J=8.9, 2.7 Hz, 1H). $^{13}$C-NMR (75.4 MHz, acetone-d6): δ: 155.8, 151.9, 143.5, 133.6, 131.7, 130.3, 129.8, 129.4, 128.6, 125.9, 125.6, 124.7, 115.6, 115.4, 106.2. ESI-MS: m/z 395.2 [M+H]$^+$; calculated mass for $C_{20}H_{14}N_2O_5S$: 394.3.

1-(m-Nitrophenylsulfonyl)-3-phenyl-5-hydroxyindole 18 has been synthesized by means of the general procedure described above, starting from compound 12 (288 mg, 0.71 mmol) and by purifying the green crude solid (290 mg) with n-Hexane/EtOAc 7/3 as eluting mixture.

19. Yield: 82% (yellow solid, 102 mg, MW 394.4, 0.30 mmol). Analytical characterization: $^1$H-NMR (400 MHz, acetone-d6): δ: 8.42-8.32 (m, 4H), 7.95 (d, J=8.9 Hz, 1H), 7.88 (s, 1H), 7.69-7.66 (m, 2H), 7.53-7.47 (m, 2H), 7.43-7.36 (m, 1H), 7.22 (d, J=2.7 Hz, 1H), 6.99 (dd, J=8.9, 2.7 Hz, 1H). $^{13}$C-NMR (75.4 MHz, acetone-d6): δ: 155.8, 151.9, 143.5, 133.6, 131.7, 130.3, 129.8, 129.4, 128.6, 125.9, 125.6, 124.7, 115.6, 115.4, 106.2. ESI-MS: m/z 389.9 [M+Na]$^+$; calculated mass for $C_{20}H_{14}FNO_3S$: 367.3.

1-(m-Fluorophenylsulfonyl)-3-phenyl-5-hydroxyindole 20 has been synthesized by means of the general procedure described above, starting from compound 14 (300 mg, 0.79 mmol) and by purifying the green crude solid (259 mg) with n-Hexane/EtOAc 75/25 as eluting mixture.

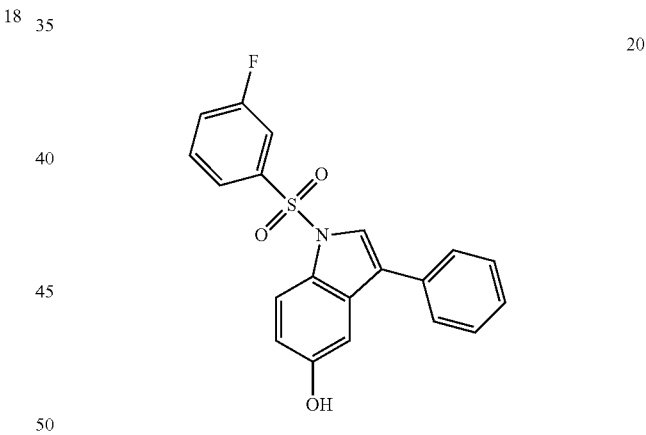

18

20

18. Yield: 73% (yellow solid, 204 mg, MW 394.4, 0.52 mmol). Analytical characterization: $^1$H-NMR (400 MHz, acetonitrile-d3): δ: 8.70-8.68 (m, 1H), 8.43-8.41 (m, 1H), 8.25-8.29 (m, 1H), 7.95 (d, J=8.9 Hz, 1H), 7.85 (s, 1H), 7.77 (dd, 1H, J=8.1, 8.1 Hz, 1H), 7.67-7.62 (m, 2H), 7.53-7.49 (m, 2H), 7.44-7.40 (m, 1H), 7.18 (d, J=2.4 Hz, 1H), 7.00 (s, 1H), 6.96 (dd, J=8.9, 2.4 Hz, 1H). $^{13}$C-NMR (75.4 MHz, acetonitrile-d3): δ: 155.8, 149.3, 140.1, 133.3, 132.4, 131.7, 130.3, 129.8, 129.5, 128.7, 125.8, 124.7, 122.6, 115.6, 115.4, 106.2. ESI-MS: m/z 395.5 [M+H]$^+$; calculated mass for $C_{20}H_{14}N_2O_5S$: 394.4.

1-(p-Fluorophenylsulfonyl)-3-phenyl-5-hydroxyindole 19 has been synthesized by means of the general procedure described above, starting from compound 13 (130 mg, 0.34 mmol) and by purifying the yellow crude solid (139 mg) with n-Hexane/EtOAc 8/2 as eluting mixture.

20. Yield: 86% (white solid, 249 mg, MW 367.3, 0.68 mmol). Analytical characterization: $^1$H-NMR (400 MHz, acetone-d6): δ: 8.40 (bs, 1H), 7.96 (d, J=8.8 Hz, 1H), 7.93-7.84 (m, 3H), 7.70-7.64 (m, 3H), 7.52-7.45 (m, 3H), 7.42-7.38 (m, 1H), 7.24 (d, J=2.0 Hz, 1H), 6.99 (dd, J=8.8, 2.0 Hz, 1H). $^{13}$C-NMR (75.4 MHz, acetone-d6): δ: 164.7, 161.4, 155.6, 140.6, 133.8, 132.7, 131.5, 129.7, 128.5, 128.4, 125.2, 124.8, 122.2, 115.6, 115.2, 114.7, 114.1, 106.3. ESI-MS: m/z 757.4 [2M+Na]$^+$; calculated mass for $C_{20}H_{14}FNO_3S$: 367.3.

1-(Phenylsulfonyl)-3-(p-N,N-dimethylaminophenyl)-5-hydroxyindole 21 has been synthesized by means of the general procedure described above, starting from compound 5 (126 mg, 0.31 mmol) and by purifying the yellow crude solid (127 mg) with n-Hexane/EtOAc 6/4 as eluting mixture.

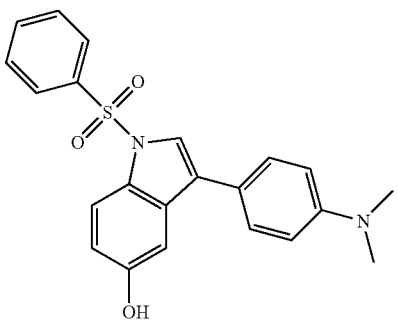

21

21. Yield: 99% (yellow solid, 120 mg, MW 392.3, 0.31 mmol). Analytical characterization: $^1$H-NMR (400 MHz, acetonitrile-d3): δ: 7.97-7.92 (m, 2H), 7.88 (d, J=8.8 Hz, 1H), 7.68 (s, 1H), 7.66-7.60 (m, 1H), 7.55-7.46 (m, 4H), 7.17 (d, J=2.7 Hz, 1H), 6.92-6.81 (m, 4H), 2.99 (s, 6H). $^{13}$C-NMR (75.4 MHz, acetonitrile-d3): δ: 155.5, 151.8, 138.8, 135.7, 132.5, 131.3, 130.8, 129.9, 128.2, 125.9, 124.1, 121.8, 116.3, 115.3, 114.1, 106.9, 41.2. ESI-MS: m/z 393.4 [M+H]$^+$; calculated mass for $C_{20}H_{14}FNO_3S$: 392.3.

4.2 General Procedure A for the Synthesis of Bicyclic Aza-Tanshinones 22-25

2-Iodoxybenzoic acid (IBX, 1.2 eq) has been added to a solution of hydroxyindole (1 eq) in EtOAc (concentration 0.17 M), under vigorous stirring at room temperature. If necessary, the reaction has been heated to 40° C. Once the reaction is completed (from 2 to 24 hours), the reaction mixture has been quickly filtered on celite. The crude has been purified by flash chromatography on silica gel (eluting mixtures: n-Hexane/EtOAc, or DCM/MeOH). The pure 1-alkyl/arylsulfonyl-3-phenyl-4,5-dioxoindoles have been obtained as amorphous solids of various color.

1-Methylsulfonyl-3-phenyl-4,5-dioxo indole 22 has been synthesized by means of the General procedure A described above, starting from compound 16 (25 mg, 0.087 mmol) and by purifying the dark crude solid (46 mg) with n-Hexane/EtOAc 1/1 as eluting mixture.

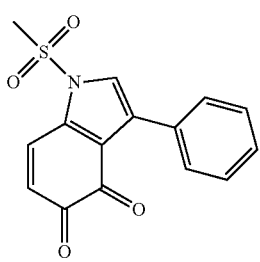

22

22. Yield: 61% (red solid, 16 mg, MW 301.31, 0.053 mmol). Analytical characterization: $^1$H-NMR (400 MHz, acetone-d6): δ: 7.96 (d, J=10.6 Hz, 1H), 7.73-7.70 (m, 2H), 7.54 (s, 1H), 7.44-7.37 (m, 3H), 6.25 (J=10.6 Hz, 1H), 3.79 (s, 3H). ESI-MS: m/z 625.1 [2M+Na]$^+$; calculated mass for $C_{15}H_{11}NO_4S$: 301.0.

1-(p-Nitrophenylsulfonyl)-3-phenyl-4,5-dioxo indole 23 has been synthesized by means of the General procedure A described above, starting from compound 17 (115 mg, 0.29 mmol) and by purifying the dark crude solid (199 mg) with n-Hexane/EtOAc 75/25 as eluting mixture.

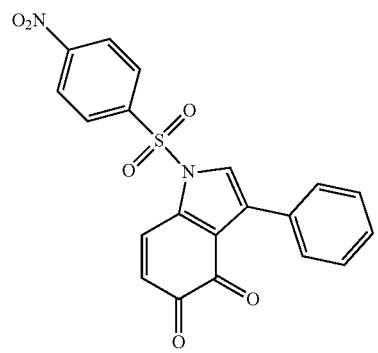

23

23. Yield 74% (red solid, 88 mg, MW 408.4, 0.022 mmol). Analytical characterization: $^1$H-NMR (400 MHz, acetone-d6): δ: 8.58-8.56 (m, 4H), 8.11 (d, J=10.6 Hz, 1H), 7.84 (s, 1H), 7.69-7.67 (m, 2H), 7.43-7.40 (m, 3H), 6.26 (d, J=10.6 Hz, 1H). ESI-MS: m/z 409.4 [M+H]$^+$; calculated mass for $C_{15}H_{11}NO_4S$: 408.4.

1-(m-Nitrophenylsulfonyl)-3-phenyl-4,5-dioxoindole 24 has been synthesized by means of the General procedure A described above, starting from compound 18 (195 mg, 0.49 mmol) and by purifying the red crude solid (322 mg) with DCM/MeOH 98/2 as eluting mixture.

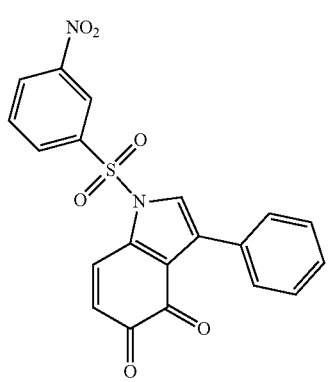

24

24. Yield 58% (red solid, 116 mg, MW 408.4, 0.028 mmol). Analytical characterization: $^1$H-NMR (400 MHz, DMSO-d6): δ: 8.93 (s, 1H), 8.73-8.64 (m, 2H), 8.08-8.01 (m, 3H), 7.68-7.65 (m, 2H), 7.46-7.38 (m, 3H), 6.26 (d, J=10.6 Hz, 1H). $^{13}$C NMR (100 MHz, DMSO-d6): δ: 180.9, 173.7, 148.5, 138.0, 136.6, 133.5, 132.5, 130.8, 130.4, 129.9, 129.1, 128.7, 128.2, 128.1, 126.8, 124.1, 122.7. ESI-MS: m/z 409.5 [M+H]$^+$; calculated mass for $C_{15}H_{11}NO_4S$: 408.4.

1-(p-Fluorophenylsulfonyl)-3-phenyl-4,5-dioxo indole 25 has been synthesized by means of the General procedure A described above, starting from compound 19 (70 mg, 0.20 mmol) and by purifying the red crude solid (135 mg) with n-Hexane/EtOAc 75/25 as eluting mixture.

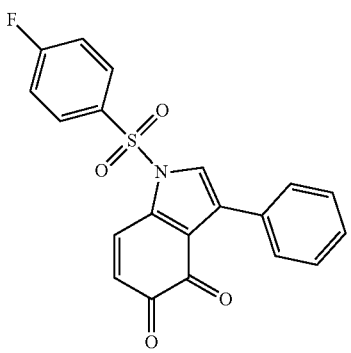

25

25. Yield 69% (red solid, 53 mg, MW 381.4, 0.014 mmol). Analytical characterization: $^1$H-NMR (400 MHz, acetone-d6): δ: 8.39-8.36 (m, 2H), 8.10 (d, J=10.6 Hz, 1H), 7.78 (s, 1H), 7.70-7.69 (m, 2H), 7.58-7.53 (m, 2H), 7.44-7.37 (m, 3H), 6.23 (d, J=10.6 Hz, 1H). $^{13}$C-NMR (75.4 MHz, acetone-d6): δ: 180.9, 173.7, 148.5, 138.0, 136.6, 133.5, 132.5, 130.8, 130.4, 129.9, 129.1, 128.7, 128.2, 128.1, 126.8, 124.1, 122.7. ESI-MS: m/z 785.4 [2M+Na]$^+$; calculated mass for $C_{20}H_{12}FNO_4S$: 381.4.

4.3 General Procedure B for the Synthesis of Bicyclic Aza-Tanshinones 26-30

2-Iodoxybenzoic acid (IBX, 1.2 eq) has been added to a solution of hydroxyindole (1 eq) in DMF (concentration 0.17 M), under vigorous stirring at room temperature. Once the reaction is completed, the mixture has been diluted with water (20 volumes with respect to DMF) and the aqueous phase has been extracted with EtOAc (several times, until the EtOAc phase is colorless). The organic phases have been washed once with brine (one third of the EtOAc volume), dried over sodium sulfate and filtered. The solvent has been removed under reduced pressure to give the crude. The crude has been purified by flash chromatography on silica gel (eluting mixtures: n-Hexane/EtOAc, or DCM/MeOH, or DCM/acetone). The pure 1-arylsulfonyl-3-aryl-4,5-dioxo indoles have been obtained as amorphous solids of various color.

1-Phenylsulfonyl-3-phenyl-4,5-dioxo indole 26 has been synthesized by means of the General procedure B described above, starting from compound 15 (1.03 g, 2.94 mmol) and by purifying the dark crude solid (1.95 g) with n-Hexane/EtOAc 6/4 as eluting mixture.

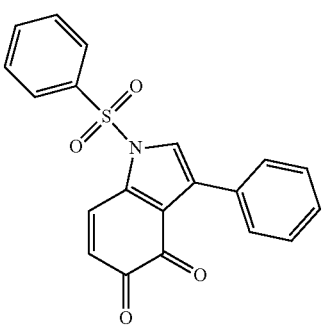

26

26. Yield 67% (red solid, 720 mg, MW 363.4, 1.98 mmol). Analytical characterization: $^1$H-NMR (400 MHz, acetone-d6): δ: 8.25-8.23 (m, 2H), 8.07 (d, J=10.5 Hz, 1h), 7.87 (tt, J=7.5, 1.2 Hz, 1H), 7.78-7.74 (m, 3H), 7.68-7.65 (m, 2H), 7.40-7.33 (m, 3H), 6.25 (d, J=10.5 Hz, 1H), 3.79 (s, 3H). ESI-MS: m/z 625.1 [2M+Na]$^+$; calculated mass for $C_{15}H_{11}NO_4S$: 301.0. $^{13}$C-NMR (75.4 MHz, acetone-d6): δ: 182.3, 174.8, 138.5, 137.9, 136.5, 132.1, 131.5, 131.3, 130.5, 129.6, 129.1, 128.9, 128.5, 127.1. ESI-MS: m/z 748.9 [2M+Na]$^+$; calculated mass for $C_{20}H_{13}NO_4S$: 363.4.

1-(m-Fluorophenylsulfonyl)-3-phenyl-4,5-dioxo indole 27 has been synthesized by means of the General procedure B described above, starting from compound 20 (206 mg, 0.56 mmol) and by purifying the red crude solid (370 mg) with DCM/MeOH 99/1 as eluting mixture.

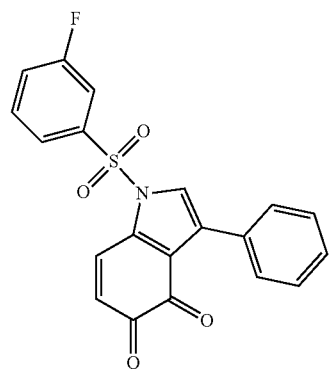

27

27. Yield 73% (red solid, 143 mg, MW 381.4, 0.037 mmol). Analytical characterization: $^1$H-NMR (400 MHz, acetone-d6): δ: 8.14-8.10 (m, 1H), 8.12 (d, J=10.6 Hz, 1H), 8.10 (J=8.2, 1.8 Hz, 1H), 7.87 (ddd, J=7.6, 4.5 Hz, 1H), 7.81 (s, 1H), 7.72-7.67 (m, 3H), 7.43-7.37 (m, 3H), 6.25 (d, J=10.6 Hz, 1H). $^{13}$C-NMR (75.4 MHz, acetone-d6): δ: 182.2, 174.0, 168.0, 138.0, 137.0, 133.6, 132.0, 131.4, 130.6, 129.6, 128.9, 127.6, 127.4, 124.7, 123.7, 115.6. ESI-MS: m/z 785.5 [2M+Na]$^+$; calculated mass for $C_{20}H_{12}FNO_4S$: 381.4.

1-phenylsulfonyl-3-(p-methoxyphenyl)-4,5-dioxo indole 28 has been synthesized by means of the General procedure B described above, starting from compound 7 (82 mg, 0.22 mmol) and by purifying the purple crude solid (164 mg) with DCM/acetone 98/2 as eluting mixture.

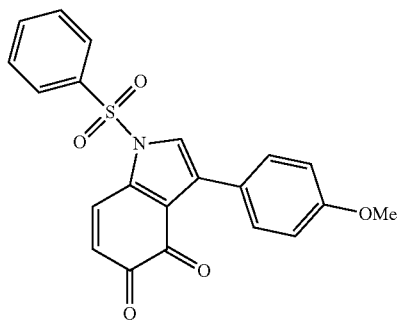

28

28. Yield 67% (red solid, 58 mg, MW 393.4, 0.015 mmol). Analytical characterization: $^1$H-NMR (400 MHz, DMSO-d6): δ: 8.26-8.23 (m, 2H), 7.95 (d, J=10.5 Hz, 1H), 7.89-7.85 (m, 1H), 7.85 (s, 1H), 7.77-7.73 (m, 2H), 7.64-7.60 (m, 2H), 6.98-6.94 (m, 2H), 6.21 (d, J=10.6 Hz, 1H), 3.80 (s, 3H). $^{13}$C-NMR (75.4 MHz, DMSO-d6): δ: 181.0, 173.8, 159.3, 136.8, 136.1, 135.9, 130.5, 129.9, 128.7, 127.6, 126.4, 123.3, 122.3, 113.5, 55.2. ESI-MS: m/z 809.5 [2M+Na]$^+$; calculated mass for $C_{21}H_{15}NO_5S$: 393.4.

1-Phenylsulfonyl-3-(m-methoxyphenyl)-4,5-dioxoindole 29 has been synthesized by means of the General procedure B described above, starting from compound 8 (108 mg, 0.29 mmol) and by purifying the dark crude solid (240 mg) with DCM/acetone 99/1 as eluting mixture.

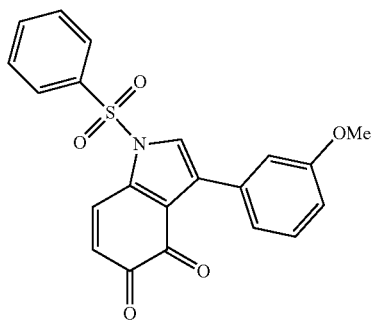

29

29. Yield 80% (red solid, 91 mg, MW 393.4, 0.023 mmol). Analytical characterization: $^1$H-NMR (400 MHz, acetone-d6): δ: 8.27-8.25 (m, 2H), 8.09 (d, J=10.6 Hz, 1H), 7.92-7.88 (m, 1H), 7.80-7.77 (m, 3H), 7.33-7.25 (m, 3H), 6.96-6.93 (m, 1H), 6.24 (d, J=10.6 Hz, 1H), 3.84 (m, 3H), $^{13}$C-NMR (75.4 MHz, acetone-d6): δ: 182.2, 175.0, 160.4, 138.4, 137.9, 136.3, 133.3, 131.5, 131.1, 130.2, 129.9, 128.5, 127.1, 124.8, 123.9, 121.7, 114.9, 55.5. ESI-MS: m/z 809.4 [2M+Na]$^+$; calculated mass for $C_{21}H_{15}NO_5S$: 393.4.

1-phenylsulfonyl-3-(p-N,N-dimethylaminophenyl)-4,5-dioxo indole 30 has been synthesized by means of the General procedure B described above, starting from compound 21 (113 mg, 0.29 mmol) and by purifying the dark crude oil (206 mg) with DCM/acetone 98/2 as eluting mixture.

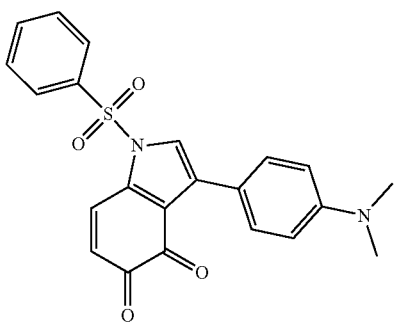

30

30. Yield 70% (red solid, 83 mg, MW 406.4, 0.020 mmol). Analytical characterization: $^1$H-NMR (400 MHz, DMSO-d6): δ: 8.25-8.23 (m, 2H), 7.95 (d, J=10.6 Hz, 1H), 7.88-7.84 (m, 1H), 7.78 (s, 1H), 7.78-7.73 (m, 2H), 7.56-7.54 (m, 2H), 6.73-6.71 (m, 2H), 6.19 (d, J=10.6 Hz, 1H), 2.94 (s, 6H). $^{13}$C-NMR (75.4 MHz, DMSO-d6): δ: 186.3, 179.1, 155.4, 142.0, 141.2, 141.0, 135.8, 135.2, 134.9, 134.5, 132.7, 131.3, 127.7, 127.4, 123.4, 116.7. ESI-MS: m/z 407.3 [M+H]$^+$; calculated mass for $C_{22}H_{18}N_2O_4S$: 406.4.

EXAMPLE 5

Synthesis of 1-Arylsulfonyl-3,7-Diaryl-4,5-Dioxo Indole (Formula I, X═C—R$_5$; R$_1$=Aryls; R$_2$, R$_3$=Aryls; R$_4$, R$_5$═H)

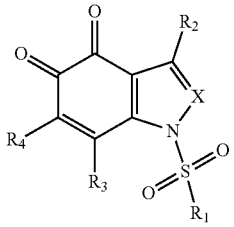

(I)

Some of the compounds referring to the structure shown above can be prepared from the above reported intermediates (Example 4) according to a synthesis reported in Scheme 5, consisting of the following step:
  a) C—C— coupling reaction catalyzed by Pd on ortho-quinones with arylboronic acids, to give compound 31.

Scheme 5

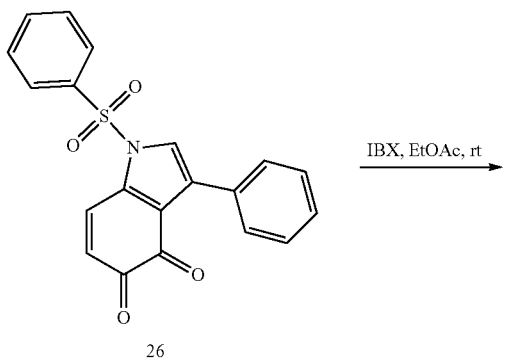

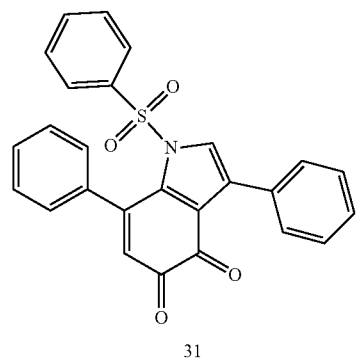

31

5.1 Procedure for the Synthesis of Compound 31

1-(phenylsulfonyl)-3-phenyl-4,5-dioxo indole 26 (118 mg, 0.32 mmol, 1.05 eq) and phenylboronic acid (38 mg, 0.31 mmol, 1 eq) have been dissolved in degassed dichloroethane (DCE, 2.3 ml). The solution has been stirred for 2 minutes and then anhydrous manganese (III) acetate (251 mg, 0.93 mmol, 3 eq) has been added. The mixture has been kept under nitrogen atmosphere, stirred at 80° C. for 5 hours and then cooled to room temperature and stirred for further 12 hours. When the reaction is completed, as monitored by TLC (eluents: n-hexane/EtOAc 75/25), DCM (4 mL), a saturated aqueous solution of NaHCO$_3$ (3 mL) and brine (3 mL) have been added in this order. The resulting solution has been extracted with DCM (4×3 mL). The pooled organic phases have been dried over sodium sulfate, filtered and evaporated under reduced pressure to give dark crude solid (71 mg). The crude has been purified by flash chromatography (eluents: n-Hexane/EtOAc, gradient from 6% to 50% EtOAc). The pure 1-(phenylsulfonyl)-3,7-diphenyl-4,5-dioxo indole 31 has been obtained as purple amorphous solid.

a) Diels-Alder cycloaddition between ortho-quinones/dienophiles and dienes, to give compound 32.

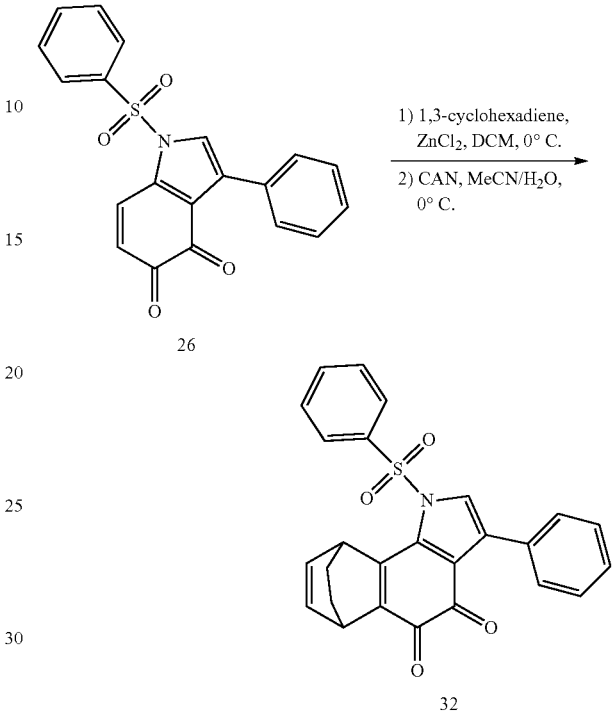

31. Yield 22% (31 mg, MW 439.4, 0.071 mmol). Analytical characterization: $^1$H-NMR (400 MHz, DMSO-d6): δ: 8.28 (d, J=8 Hz, 2H), 7.97 (s, 1H), 7.87 (m, 2H), 7.77 (t, J=8 Hz, 2H), 7.71 (dd, J=8.0, 4.0 Hz, 2H), 7.48 (d, J=4 Hz, 2H), 7.37-7.46 (m, 6H). $^{13}$C-NMR (75.4 MHz, DMSO-d6): δ: 179.5, 173.4, 137.0, 136.8, 136.0, 134.9, 130.9, 130.6, 128.7, 128.3, 128.1, 127.6, 125.0, 123.8, 121.3. ESI-MS: m/z 440.6 [M+H]$^+$; calculated mass for C$_{26}$H$_{17}$NO$_4$S: 439.4.

EXAMPLE 6

Synthesis of 3-Aryl-1-Arylsulfonyl-4,5-Dioxo-6,9-Ethanbenzo[g]indoles (Formula II, X=C—R$_5$; R$_1$=Aryls; R$_2$=Aryls; R$_5$=H; Cy=Annulated Fused Cyclohexenes

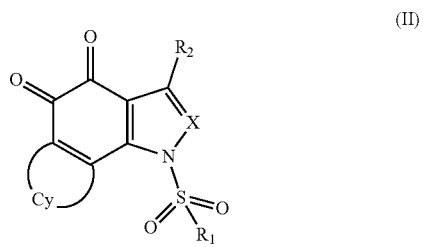

Some of the compounds referring to the structure shown above can be prepared from the above reported intermediates (Example 4) according to a synthesis reported in Scheme 6, consisting of the following reaction:

6.1 Procedure for the Synthesis of Compound 32

1-Phenylsulfonyl-3-phenyl-4,5-dioxoindole 26 (50 mg, 0.14 mmol, 1 eq) has been dissolved in anhydrous DCM (0.8 mL) and cooled to 0° C. under stirring in nitrogen atmosphere. 1,3-Cyclohexadiene (65 mL, 0.69 mmol, 5 eq) and ZnCl$_2$ (catalytic amount) have been added, observing a color change (from red to brown) in the solution. After 10 minutes, the TLC monitoring (eluents: n-Hexane/EtOAc 6/4) showed the disappearance of 26. Then brine (1 mL) was added to quench the reaction, which has then been left to recover up to room temperature. The reaction mixture has been diluted with brine (10 mL) and extracted with DCM (2×15 mL). The pooled organic phases have been washed with brine (20 mL) and dried over sodium sulfate. A dark brown residue (66 mg) has been purified by chromatography (eluents: n-Hexane/EtOAc 7/3), obtaining 55 mg of a ≈1:1 mixture of the desired compound 32 and of its reduced/phenolic isomer.

The mixture obtained from chromatography has been dissolved in MeCN (3 mL) at 0° C. under vigorous stirring. A 0.08 M aqueous solution of cerium ammonium nitrate (CAN) (3 mL) has been divided into two aliquots and each of these has been added dropwise under stirring (the second addition started 15 minutes after the end of the first). After 10 minutes, the TLC (eluents: n-Hexane/EtOAc 7/3) showed the disappearance of the reduced/diphenolic compound. The reaction mixture has been quenched with water (10 mL) and extracted with EtOAc (2×15 mL). The pooled organic phases have been washed (brine, 30 mL), dried over sodium sulfate and evaporated under reduced pressure. The resultant dark crude (55 mg) has been purified by chromatography (eluent: pure DCM), obtaining the pure 3-Phenyl-1-phenyl-sulfonyl-4,5-dioxo-6,9-ethanbenzo[g]indole 32 as purple solid.

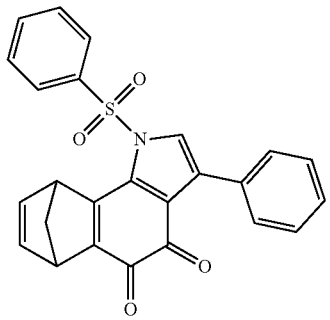

32

32. Yield (two steps) 69% (43 mg, MW 441.5, 0.097 mmol). Analytical characterization: $^1$H-NMR (400 MHz, acetone-d6): δ: 8.12-8.09 (m, 2H), 7.91 (tt, J=7.5, 1.2 Hz, 1H), 7.84-7.79 (m, 2H), 7.68 (s, 1H) 7.62-7.59 (m, 2H), 7.42-7.34 (m, 3H), 6.41-6.37 (m, 1H), 6.09-6.05 (m, 1H), 4.83-4.80 (m, 1H), 4.22-4.19 (m, 1H), 1.37-1.11 (m, 4H). $^{13}$C-NMR (100 MHz, acetone-d6): δ: 178.8, 177.0, 176.9, 140.3, 139.4, 136.2, 136.0, 133.0, 131.34, 129.8, 128.8, 127.8, 127.1, 39.5, 35.2, 25.1, 24.8. ESI-MS: m/z 441.5 [M+H]$^+$; calculated mass for $C_{26}H_{19}NO_4S$: 904.9 [2M+Na]$^+$.

EXAMPLE 7

Synthesis of 3-Aryl-1-Arylsulfonyl-4,5-Dioxo-1H-naphtho[2,3-g]indoles (Formula II, X=C—R$_5$; R$_1$=Aryls; R$_2$=Aryls; R$_5$=H; Cy=Fused Substituted Naphthalenes)

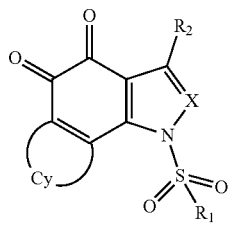

(II)

Some of the compounds referring to the structure shown above can be prepared from the above reported intermediates (Example 4) according to a synthesis reported in Scheme 7, comprising the following reaction:

a) Tamura-Diels Alder cycloaddition between ortho-quinones/dienophiles and phthalic anhydrides, to give compound 33.

Scheme 7

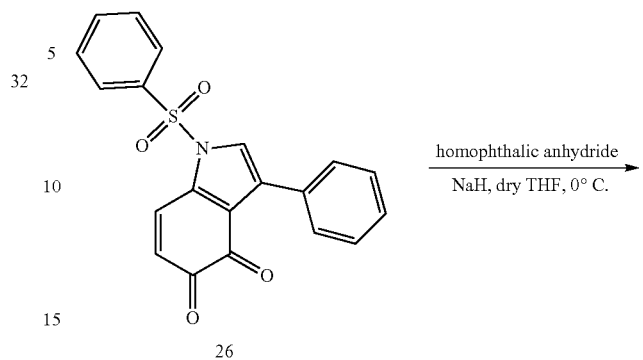

7.1 Procedure for the Synthesis of Compound 6-hydroxy-3-phenyl-1-(phenylsulfonyl)-1H-naphtho[2,3-g]indole-4,5-dione (33)

A mixture of homophthalic anhydride (44 mg, 0.28 mmol, 1 eq) and 60% NaH (12 mg, 0.30 mmol, 1.1 eq) in anhydrous THF has been vigorously stirred under nitrogen at 0° C. for 10 minutes. Then, a solution of 1-phenylsulfonyl-3-phenyl-4,5-dioxo indole 26 (100 mg, 0.28 mmol, 2 eq) in anhydrous DMF (final concentration of 26: 0.08M) has been slowly added under stirring. After 10 minutes the temperature has been slowly raised to room temperature. The reaction has been monitored by TLC (eluents: n-Hexane/EtOAc 6:4). When the reaction was completed, the solution has been quenched with a saturated solution of NH$_4$Cl (15 mL). Then 3% aqueous HCl (3 mL) has been added, and the reaction mixture has been extracted with DCM until the aqueous phase was colorless. The pooled organic phases have been dried over sodium sulfate, and the solvent evaporated under reduced pressure providing 115 mg of red crude solid. The resultant crude has been purified by flash chromatography on silica gel (eluents: DCM/MeOH 8/2), to give the pure 6-hydroxy-3-phenyl-1-(phenylsulfonyl)-4,5-dioxo-1H-naphtho[2,3-g]indole 33 as red amorphous solid.

33

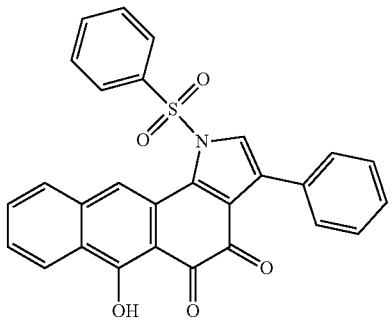

33. Yield 68% (90 mg, MW 479.5, 0.19 mmol). Analytical characterization: ESI-MS: m/z 479.5 [M+H]$^+$; calculated mass for $C_{28}H_{17}NO_5S$: 982.5 [2M+Na]$^+$.

EXAMPLE 8

8.1 In-Vitro Inhibition of HuR-mRNA Interactions: REMSA and AlphaScreen protocols Experimental Protocol The full encoding sequence for human HuR/ELAVL1 gene (NM001419) has been amplified from cDNA obtained by retro-transcription from RNA of MCF7 cells and inserted into the pCMV6-AC-Myc-His PrecisionShuttle vector (Origene Technologies). The pCMV6-HuR recombinant vector has been transfected into HEK293T cells by using the transfection reagent Lipofectamine® 2000 (Life Technologies) according to the manufacturer protocol. HEK293T cells have been cultured in a complete medium (10% DMEM, 10% FBS, 2 mM Glutamine, 100 units/ml penicillin+100 μg/ml streptomycin) in humidified 5% $CO_2$ atmosphere at 37° C. Cells have been harvested 48 hours after the transfection and sonicated (amplitude 90 Hz for 3 cycles of 15 seconds, break for 1 minute between the cycles) at 4° C. in W buffer (20 mM NaH2PO4, 0.5 M NaCl, 20 mM imidazole, pH 7.4) in addition to the Protease Inhibitor Cocktail (Sigma-Aldrich; P8340).

The HuR-Myc-His recombinant protein (rHuR) has been purified by affinity chromatography with HisTrap HP resin (GE Healthcare; 17-5248-01) and eluted in imidazole gradient between 62.5 and 500 mM. rHuR has been dialyzed by means of Zeba™ Spin Desalting Columns (Thermo Scientific; 89890), following the recommended protocol, in order to remove the imidazole residues and has been stored at −80° C. in S buffer (20 mM $NaH_2PO_4$, 100 mM NaCl, 50 mM glycine, 10% glycerol, pH 7.5).

Two types of assay have been performed, in order to define the profile of the aza-tanshinones and their inhibitory activity. REMSA (RNA-EMSA, RNA electrophoresis mobility shift assay) in 5% polyacrylamide gel requires the use of a RNA fluorescent probe (5'-Cy3-AUUAUUUAUUAUUUAUUUAUUAUUUA), while the AlphaScreen assay required a RNA 5'-biotinylated probe (BiTNF, 5'-AUUAUUUAUUAUUUAUUUAUUAUUUA). Both assays have been performed as a function of the increase of RNA probe amount, until achieving the saturation conditions (44). The dissociation constants at the equilibrium (Ki) of the compounds have been fitted according to the 1-site competition model in GraphPad Prism®, version 5.0 (GraphPad Software, Inc., San Diego, Calif.), by keeping constant the RNA concentrations RNA (50 nM) and the Kd of the reactions at the equilibrium 2.5 nM). $IC_{50}$ values have been obtained by means of non-linear regression of the fit of the log(dose) response by using the same software. Time-course experiments have been carried out by means of the simultaneous reaction of ligands and compounds, or by means of pre-incubation of the compounds with rHuR or RNA. Dissociation experiments have been carried out within 30 minutes from the pre-incubation of 1 nM of rHuR and 50 nM of RNA in addition to beads ("Ligands+beads"), before the addition of the compounds. In order to exclude possible interferences of the beads on the dissociations kinetics, the proteins and the RNA ("Ligands") have been pre-incubated for 30 minutes, then the compounds have been added, at the indicated concentrations and, finally, the beads have been added. The curves have been fitted according to the kinetics of the competitive binding model in GraphPad software, by keeping constant the $k_{on}$ (2.76±0.56*10^6M$^{-1}$ min$^{-1}$) and $k_{off}$ (0.007±0.005 min$^{-1}$).

Results

Ten compounds, including the DHTS standard, have been tested and confirmed to have inhibitory activity in the AlphaScreen assays compared to DHTS (Table 1).

TABLE 1

| | $IC_{50}$ | Complete Ki |
| --- | --- | --- |
| DHTS | 149 ± 34 nM | 3.74 ± 1.63 nM |
| 26 | 59 ± 27 nM | 0.66 ± 0.21 nM |
| 32 | 121 ± 55 nM | — |
| 25 | 254 ± 22 nM | — |
| 23 | 241 ± 42 nM | |
| 24 | 342 ± 64 nM | |
| 28 | 287 ± 30 nM | |
| 27 | 251 ± 31 nM | |
| 29 | 352 ± 57 nM | |
| 22 | 181 ± 21 nM | |

While the aza-tanshinones of the invention have been confirmed to have potent inhibitory activity of the HuR-mRNA interaction, their potency varies as a function of their chemical structure, with clear indication of structure-activity relationships (SARs) between the different congeners. In particular, the $IC_{50}$ values in Table 1 show that compound 26 is the most effective aza-tanshinone in preventing the HuR-RNA binding at low nanomolar concentrations. The natural compound DHTS is slightly less potent with respect to aza-tanshinone 26. The potency of compound 26 has been confirmed by using the REMSA-type assay.

Saturation experiments of the competitive binding at the equilibrium carried out by means of AlphaScreen assays, by using a $K_d$ of 2.5 nM for the HuR-RNA interaction, determine a sub-nanomolar dissociation constant (Table 1, $K_i$) for compound 26, confirming it as the most effective modulator/inhibitor of the mRNA-HuR binding.

8.2 Cytotoxicity in a Tumor Cell Line—Test of Aza-Tanshinones on Four Cell Lines Experimental Protocol Tumor cell lines of metastatic breast cancer (MDA-MB-231), breast cancer (MCF7), human monocytic leukemia (THP-1) and pancreatic carcinoma (PANC-1) have been cultured in a complete DMEM or RPMI 1640 (Gibco Life Technologies) supplemented with 10% fetal bovine serum (FBS, Lonza), 2 mM L-glutamine and 100 U/ml penicillin-streptomycin (Lonza). The cell lines have been cultured at 37° C. in 5% $CO_2$ and have been regularly tested for *Mycoplasma* contamination. The viability has been measured by means of alamar Blue assay (Thermo Fisher) under treatment for 24 hours with nanomolar to micromolar doses of aza-tanshinones. The mean viability and the standard deviation (SD) per each test compound have been obtained from the dose-response curves for triple doses (0.01, 0.1, 1. 10. 50 µM) in comparison with the control vehicle (DMSO).

Results

|  | MDA-MB-231 | | | | MCF7 | | | |
| --- | --- | --- | --- | --- | --- | --- | --- | --- |
|  | 50 µM | | 10 µM | | 50 µM | | 10 µM | |
|  | Viability | SD | Viability | SD | Viability | SD | Viability | SD |
| 23 | 0.80 | 0.019 | 1.04 | 0.009 | 0.66 | 0.048 | 1.00 | 0.006 |
| 25 | 0.50 | 0.011 | 1.03 | 0.019 | 0.63 | 0.008 | 1.00 | 0.044 |
| 24 | 0.36 | 0.032 | 0.94 | 0.017 | 0.54 | 0.007 | 1.00 | 0.053 |
| 28 | 0.57 | 0.021 | 1.06 | 0.020 | 0.75 | 0.040 | 0.91 | 0.030 |
| 27 | 0.51 | 0.008 | 1.03 | 0.010 | 0.79 | 0.024 | 1.08 | 0.086 |
| 32 | 0.28 | 0.009 | 1.00 | 0.008 | 0.14 | 0.019 | 1.09 | 0.016 |

|  | PANC-1 | | | | THP1 | | | |
| --- | --- | --- | --- | --- | --- | --- | --- | --- |
|  | 50 µM | | 10 µM | | 50 µM | | 10 µM | |
|  | Viability | SD | Viability | SD | Viability | SD | Viability | SD |
| 23 | 0.36 | 0.009 | 0.92 | 0.007 | 0.31 | 0.005 | 0.98 | 0.019 |
| 25 | 0.29 | 0.009 | 1.00 | 0.007 | 0.35 | 0.005 | 1.00 | 0.035 |
| 24 | 0.20 | 0.005 | 0.91 | 0.011 | 0.27 | 0.017 | 1.00 | 0.039 |
| 28 | 0.32 | 0.021 | 0.90 | 0.016 | 0.46 | 0.031 | 1.05 | 0.054 |
| 27 | 0.20 | 0.008 | 1.02 | 0.020 | 0.32 | 0.014 | 0.83 | 0.005 |
| 32 | 0.15 | 0.002 | 0.85 | 0.024 | 0.00 | 0.002 | 0.55 | 0.030 |

Among the tested aza-tanshinones, compounds 32, 24 and 27 caused more cytotoxic effects at 50 µM on all the tested tumor cell lines. When tested at 10 µM, only compound 32 induced the cell death greater than 20% in THP-1 cells.

Our aza-tanshinones showed moderate to good cytotoxicity in the medium-low micromolar range, after treatment for 24 hours. Again, their potency varies as a function of their chemical structure, with indication of the structure-activity relationships (SARs) between the congeners.

8.3 Cytotoxicity of Aza-Tanshinone 26 on Tumor Cell Lines

Experimental Protocol

The group of cell lines used in Paragraph 8.2, with the addition of the tumor cell lines of the metastatic breast cancer SK-BR-3 and of the colon adenocarcinoma SW-480, has been used to measure the $IC_{50}$/cytotoxicity potency of compound 26. The viability assays have been performed as shown in Paragraph 8.2.

Results

Aza-tanshinone 26 has been selected, among the other compounds, to carry out the evaluation of its toxicity on a group of tumor cell lines. The observed $IC_{50}$ values are reported in Table 3.

TABLE 3

|  | IC50 [µM] | % cell death |
| --- | --- | --- |
| MDA-MB-231 | 1.57 ± 0.04 | 66 |
| MCF7 | 3.85 ± 0.08 | 71 |

TABLE 3-continued

|  | IC50 [µM] | % cell death |
| --- | --- | --- |
| SK-BR-3 | 5.18 ± 0.11 | 57 |
| SW480 | 4.81 ± 0.23 | 62 |

TABLE 3-continued

|  | IC50 [µM] | % cell death |
| --- | --- | --- |
| PANC-1 | 6.27 ± 0.07 | 49 |
| THP-1 | 9.77 ± 0.15 | 52 |

The observed $IC_{50}$ values clearly show a general potency of cytotoxicity, which supports the concept of therapeutic usefulness of aza-tanshinones against different kinds of cancer.

8.4 Downregulation of TNF in Tumor Cell Lines—Aza-Tanshinone 26

Experimental Protocol

MCF-7 breast cancer cells (5*10^4/well) have been seeded in 6-well plates and cultured under standard conditions for 24 hours. The MCF-7 cells have then been treated for 3 hours in a complete medium with compound 26, or with DMSO/control vehicle. Three hours of treatment with DHTS in the MCF-7 cells have been enough to observe HuR-dependent post-transcriptional effects (44), whereby the same experimental conditions have been used here, including the co-treatment with lipopolysaccharide (LPS) as positive control to induce the TNF expression.

Results

Compound 26 has been administered to the MCF-7 cells and its effect on the TNF mRNA is shown in Table 4.

TABLE 4

|  | TNF |
|---|---|
| LPS+DMSO | 1.62 |
| SD | 0.04 |
| LPS+26 | 1.00 |
| SD | 0.06 |
| RNA amount | 62% |

Compound 26 reduced the expression of TNF in MCF-7 cells. In other words, after 3 hours a reduction of the TNF mRNA of 35%±1.2 with respect to the control has been measured.

8.5 Downregulation of Endogenous Cytokines in Human Macrophages—Aza-Tanshinone 26

Experimental Protocol

THP-1 human leukemia monocytes ($5*10^4$/well) have been seeded in a 6-well plate and cultured under standard conditions for 24 hours as already described. The mRNA total levels for a group of cytokines have been quantified by means of standard quantitative real-time PCR (Q-RT-PCR). Two-way ANOVA has been applied for a statistical significance of the effects of compound 26 on the decrease of the mRNA of the cytokines.

Results

Compound 26 has been tested on THP-1 cells to evaluate its impact on target HuR mRNA and its effects are shown in Table 5 (they are expressed as comparison between LPS-DMSO (control) and LPS-compound 26-treated cells).

TABLE 5

|  | LPS DMSO | SD | LPS 26 | SD | P Value |
|---|---|---|---|---|---|
| CCL2 | 1 | 0.158 | 0.88 | 0.179 | NS |
| CCL5 | 1 | 0.411 | 0.51 | 0.244 | 0.015 |
| CCL8 | 1 | 0.061 | 0.00 | 0.079 | 0.042 |
| IFNA1 | 1 | 0.500 | 0.46 | 0.152 | 0.015 |
| IFNB1 | 1 | 0.040 | 0.33 | 0.309 | 0.027 |
| IFNG | 1 | 0.053 | 0.38 | 0.170 | 0.011 |
| IL10 | 1 | 0.043 | 0.16 | 0.030 | 0.031 |
| IL13 | 1 | 0.316 | 0.53 | 0.092 | 0.006 |
| IL15 | 1 | 0.562 | 0.91 | 0.045 | 0.017 |
| IL17A | 1 | 0.032 | 0.30 | 0.231 | 0.013 |
| IL18 | 1 | 0.061 | 0.36 | 0.036 | 0.020 |
| IL19 | 1 | 0.381 | 0.01 | 0.086 | 0.040 |
| IL1A | 1 | 0.335 | 1.04 | 0.093 | 0.007 |
| IL1B | 1 | 0.320 | 0.22 | 0.234 | 0.027 |
| IL2 | 1 | 0.022 | 1.18 | 0.152 | NS |
| IL4 | 1 | 0.036 | 0.82 | 0.096 | 0.006 |
| IL7 | 1 | 0.140 | 0.56 | 0.168 | 0.011 |
| IL8 | 1 | 0.020 | 0.15 | 0.021 | 0.026 |
| TNF | 1 | 0.241 | 0.38 | 0.080 | 0.014 |

The results show that TNF, IL13, IL7, IL17A, IL15, IFNG, IFNA1 and CCL5 are, under a cell situation of global reduction of mRNA and among the tested cytokines, those most markedly decreased by the treatment with compound 26.

8.6 Inhibition of Binding Intracellular Activity with RNA of the HuR Protein—Aza-Tanshinone 26

Experimental Protocol

The RNA ImmunoPrecipitation (RIP) analysis on HuR regulated transcript has been used to determine the number of copies of TNF mRNA, beta-catenin, IL3, IL6, and IL17B bound to HuR. Specifically, five*$10^6$ MCF7 cells/sample have been used in each RIP experiment carried out by incubating the cell lysate with anti-HuR antibody and precipitating the protein-RNA complexes by using protein G-coupled magnetic beads (44). The experiments have been carried out without cross-linking steps and by using 0.8 µg/ml of anti-HuR antibody or mouse IgG isotype (negative control). The TRIzol reagent has been directly added into the beads for the isolation of HuR bound to the RNA. The enrichment has been calculated by means of the equation $2e-\Delta Ct$, $\Delta Ct$=target mRNA IP HuR/(target mRNA IgG).

Results

The RIP on transcripts regulated by HuR shown that the number of copies of TNF mRNA, beta-catenin, IL3, IL6, and IL17B bound by HuR in the presence of compound 26 is consistently decreased. The variation is expressed as fold change with respect to the DMSO control in Table 6.

TABLE 6

|  | Fold change to LPS DMSO |
|---|---|
| TNF | 0.36 ± 0.09 |
| Beta-Catenin | 0.47 ± 0.05 |
| IL3 | 0.27 ± 0.08 |
| IL6 | 0.02 ± 0.01 |
| IL17B | 0.73 ± 0.17 |

The effects vary depending on the target mRNA/transcribed proteins, but an effect has been seen in each of the monitored proteins, thus confirming the previously observed/reported effects on the mRNAs.

8.7 Pro-Apoptotic Effects in the Tumor Cell Lines—Compound 26

Experimental Protocol

MDA-MB-231, MCF7, SW480 and PANC-1 cell lines have been cultured as reported in Paragraph 8.2. In order to quantify the activation of apoptosis, the amount of cleaved fragments of caspase 7 and caspase 9 has been measured by means of Western blot analysis on extracts of cell treated for 24 hours with compound 26 in biological triplicates.

Results

In treated cells, the apoptotic activation was clearly visible after 24 hours by using an amount as low as 0.1 µM of aza-tanshinone 26. This has been observed by means of densitometric analysis of cleaved fragments of caspase 7 and 9, which have been normalized in each different cell line with respect to the control levels treated with DMSO (Table 7).

TABLE 7

|  | Caspase 7 | Caspase 9 |
|---|---|---|
| MDA-MB-231 | 1.9 ± 0.2 | 2.3 ± 0.3 |
| MCF7 | 1.4 ± 0.3 | 1.8 ± 0.2 |
| SW480 | 1.6 ± 0.2 | 1.6 ± 0.1 |
| PANC-1 | 1.3 ± 0.1 | 1.3 ± 0.5 |

Fold Change Normalized Over the Control Levels.

The increase of apoptosis caused by compound 26 on each tested cell line clearly shows its general pro-apoptotic effect.

8.8 Anti-Migration Effects on Invasive Tumor Cell Lines—Aza-Tanshinone 26

Experimental Protocol

Migration assays have been carried out by using the xCELLigence RTCA DP Instrument (Roche) by seeding 5,000 cells/well at t0 in CIM-Plates-16 (Roche), using the 1% FBS medium (THP1 conditions) in the lower chamber and MDA-MB-231 cells seeded in the same way in the upper chamber. The ability of the MDA-MB-231 cells to migrate depends also on the presence of cytokines regulated by HuR in the surrounding environment.

Scratch assays have been carried out on 6-well plates and, after treatment for 24 hours with aza-tanshinone 26, the empty area of the scratched wells has been calculated by using the ImageJ software. The experiments have been carried out in duplicate.

Results

The real-time analysis assays of the cells demonstrated that compound 26 has anti-chemotactic potential using the THP1-conditioned medium and the migration of MDA-MB-231 cells as quantitative parameter (Table 8). Aza-tanshinone 26 shows a dose-dependent inhibition of the trans-well migration of the tumor cells, as calculated through the corresponding maximum values in Table 8 with respect to the control (LPS) and the t1/2 values representing the migration hindrance of the cells as a function of time.

TABLE 8

|  | no FBS | LPS | 26 1 µM | 26 5 µM |
|---|---|---|---|---|
| T½ (hr) | 20.43 ± 0.16 | 29.28 ± 0.17 | 36.04 ± 0.15 | 21.55 ± 0.26 |
| Maximum | 0.04411 | 3.053 | 1.246 | 0.3311 |
| Minimum | 0.01643 | 0.7176 | 0.1057 | 0.1416 |
| $R^2$ | 0.8513 | 0.8410 | 0.8548 | 0.6957 |

Moreover, the scratch assays carried out with MDA-MB-231 and PANC cells confirmed the dose-dependent inhibition of compound 26 on the intrinsic migration ability of these tumor cells (Table 9).

TABLE 9

|  | DMSO | 26 1 µM | 26 5 µM |
|---|---|---|---|
| PANC1 | 1 ± 1.52 | 38 ± 7 | 32 ± 0.01 |
| MDA-MB-231 | 35 ± 1.92 | 45 ± 4 | 45 ± 1 |

Both types of assay clearly show that compound 26 prevents the ability of tumor cells to respond to chemotactic environmental stimuli, with corresponding inhibition of their intrinsic migration ability.

The invention claimed is:
1. A compound of formula (I)

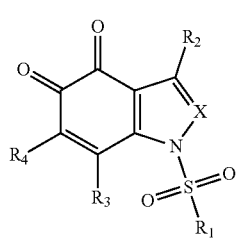

(I)

or a salt, thereof, wherein:

$R_1$ is:
- $C_{1-8}$ alkyl or heteroalkyl; $C_{2-6}$ alkenyl or heteroalkenyl; $C_{2-6}$ alkynyl or heteroalkynyl, all of them optionally substituted;
- aryl, alkylaryl, heteroaryl, or alkylheteroaryl, all of them being optionally substituted;

$R_2$, $R_3$, $R_4$ are, each independently:
- a hydrogen atom;
- $C_{1-8}$ alkyl or heteroalkyl; $C_{2-6}$ alkenyl or heteroalkenyl; $C_{2-6}$ alkynyl or heteroalkynyl, all of them being optionally substituted;
- aryl, alkylaryl, heteroaryl, or alkylheteroaryl, all of them being optionally substituted;
- or $R_3$ and $R_4$, together with the carbon atoms to which they are bound, form a 5 or 6 membered cycloalkyl, cycloheteroalkyl, aryl or heteroaryl ring being optionally substituted, being optionally fused with one or more other rings;

X is C—$R_5$ or N;

$R_5$ is:
- a hydrogen atom;
- $C_{1-6}$ alkyl or heteroalkyl; $C_{2-6}$ alkenyl or heteroalkenyl; $C_{2-6}$ alkynyl or heteroalkynyl, all of them being optionally substituted.

2. The compound according to claim 1, wherein the alkyl, alkenyl and alkynyl group is selected from methyl, ethyl, propyl, isopropyl, butyl, tert-butyl, ethenyl, propenyl, isopropenyl, butenyl, isobutenyl, ethenyl, ethynyl, propynyl and butynyl, all of them being optionally substituted.

3. The compound according to claim 1, wherein the aryl group is selected from optionally substituted phenyl and naphthyl.

4. The compound according to claim 1 wherein the optionally substituted groups are substituted with one or more halogen, alkoxy, hydroxyl, alkylhydroxyl, amine, substituted amine, alkylamine, amide, alkylamide, carboxyl, ester, cyano, nitro, oxo, thioxo and trifluoromethyl.

5. The compound according to claim 1, wherein $R_1$ is selected from optionally substituted alkyl or phenyl.

6. The compound according to claim 1, wherein $R_2$ is selected from hydrogen or an optionally substituted alkyl or phenyl group.

7. The compound according to claim 1, wherein X is a CH group or a nitrogen atom.

8. A pharmaceutical composition comprising at least one compound of formula (I) as defined in claim 1, in combination with at least one pharmaceutically acceptable carrier.

9. The compound according to claim 1, wherein
the alkyl, alkenyl and alkynyl group is selected from methyl, ethyl, propyl, isopropyl, butyl, tert-butyl, ethenyl, propenyl, isopropenyl, butenyl, isobutenyl, ethenyl, ethynyl, propynyl and butynyl, all of them being optionally substituted; and
the aryl group is selected from optionally substituted phenyl and naphthyl.

10. The compound according to claim 1, wherein
$R_1$ is selected from optionally substituted alkyl or phenyl;
$R_2$ is selected from hydrogen or an optionally substituted alkyl or phenyl group; and
the alkyl, alkenyl and alkynyl group is selected from methyl, ethyl, propyl, isopropyl, butyl, tert-butyl, ethenyl, propenyl, isopropenyl, butenyl, isobutenyl, ethenyl, ethynyl, propynyl and butynyl, all of them being optionally substituted.

11. The compound according to claim 1 wherein
the aryl group is selected from optionally substituted phenyl and naphthyl; and
X is a CH group or a nitrogen atom.

* * * * *